United States Patent
Grant et al.

(10) Patent No.: US 10,849,553 B2
(45) Date of Patent: Dec. 1, 2020

(54) SYSTEMS AND METHODS FOR PROCESSING SONIFIED BRAIN SIGNALS

(71) Applicant: CeriBell, Inc., Mountain View, CA (US)

(72) Inventors: Alexander Grant, Redwood City, CA (US); Chris Chafe, Woodside, CA (US); Josef Parvizi, Palo Alto, CA (US); Jianchun Yi, San Jose, CA (US); Raymond Woo, Los Altos, CA (US); Xingjuan Chao, Palo Alto, CA (US)

(73) Assignee: CeriBell, Inc., Mountain View, CA (US)

( * ) Notice: Subject to any disclaimer, the term of this patent is extended or adjusted under 35 U.S.C. 154(b) by 0 days.

(21) Appl. No.: 16/367,040

(22) Filed: Mar. 27, 2019

(65) Prior Publication Data

US 2020/0305786 A1 Oct. 1, 2020

(51) Int. Cl.
| | | |
|---|---|---|
| *A61B 5/04* | (2006.01) | |
| *A61B 5/00* | (2006.01) | |
| *A61B 5/0402* | (2006.01) | |
| *G10L 25/51* | (2013.01) | |
| *A61B 5/0488* | (2006.01) | |
| *A61B 5/0496* | (2006.01) | |
| *H04R 3/04* | (2006.01) | |
| *A61B 5/0476* | (2006.01) | |

(52) U.S. Cl.
CPC ............ *A61B 5/486* (2013.01); *A61B 5/0402* (2013.01); *A61B 5/0476* (2013.01); *A61B 5/0488* (2013.01); *A61B 5/0496* (2013.01); *A61B 5/7415* (2013.01); *G10L 25/51* (2013.01); *H04R 3/04* (2013.01)

(58) Field of Classification Search
None
See application file for complete search history.

(56) References Cited

U.S. PATENT DOCUMENTS

| 3,859,988 A | 1/1975 | Lencioni, Jr. |
| 4,141,351 A | 2/1979 | James et al. |

(Continued)

FOREIGN PATENT DOCUMENTS

| DE | 3246261 A1 | 3/1984 |
| WO | WO-2017172742 A1 | 10/2017 |

*Primary Examiner* — Erica S Lee
(74) *Attorney, Agent, or Firm* — Wilson Sonsini Goodrich and Rosati, P.C.

(57) ABSTRACT

Systems and methods for sonifying electrical signals obtained from a living subject, particularly EEG signals, are disclosed. A time-domain signal representing the activity of an organ is obtained. A voltage of the time-domain signal over a time block is determined. An acoustic signal based on the time-domain signal over the time block is produced. The acoustic signal comprises one or more audibly discernible variations representative of the activity of the organ. If the determined voltage is over a threshold voltage, the time-domain signal is squelched over at least a portion of the time-block as the acoustic signal is produced. The time-domain signal can be squelched by ramping down the signal as an input to produce the acoustic signal. The frequency spectrum of the acoustic signal can also be adjusted as it is produced, such as by flattening the signal and/or attenuating high frequencies along the frequency spectrum of the signal.

24 Claims, 24 Drawing Sheets

(56) References Cited

U.S. PATENT DOCUMENTS

| | | | |
|---|---|---|---|
| RE30,502 E | 2/1981 | Lencioni, Jr. | |
| 5,921,939 A | 7/1999 | Danielsson et al. | |
| 6,175,762 B1 * | 1/2001 | Kirkup | A61B 5/0482 600/544 |
| 7,020,513 B2 | 3/2006 | Faisandier | |
| 7,171,265 B2 | 1/2007 | Hoium et al. | |
| 7,676,263 B2 | 3/2010 | Harris et al. | |
| 8,086,300 B2 | 12/2011 | Herlerkson | |
| 8,271,078 B2 | 9/2012 | Rytky | |
| 9,113,805 B2 | 8/2015 | Mortara | |
| 9,615,761 B2 | 4/2017 | Chi et al. | |
| 9,622,673 B2 | 4/2017 | Zhang et al. | |
| 9,888,884 B2 | 2/2018 | Chafe et al. | |
| 2008/0249430 A1 * | 10/2008 | John | A61B 5/0476 600/544 |
| 2011/0306894 A1 | 12/2011 | Spaulding et al. | |
| 2013/0324878 A1 | 12/2013 | Chafe et al. | |
| 2015/0038869 A1 | 2/2015 | Simon et al. | |
| 2015/0150520 A1 * | 6/2015 | Chafe | A61B 5/7415 600/483 |
| 2015/0241505 A1 | 8/2015 | Freeman et al. | |
| 2015/0327811 A1 | 11/2015 | Mortara | |
| 2017/0020405 A1 | 1/2017 | Peterson | |
| 2017/0086744 A1 | 3/2017 | Sunderland | |
| 2017/0135640 A1 | 5/2017 | Gunasekar et al. | |
| 2017/0251969 A1 * | 9/2017 | Barnett | A61B 5/4094 |
| 2017/0258402 A1 | 9/2017 | Acquista et al. | |
| 2017/0281014 A1 | 10/2017 | Von et al. | |

\* cited by examiner

612 — For each respective representation of an acoustic signal, concurrently generate a plurality of acoustic parameters, including a plurality of time-varying acoustic parameters.

One or more of the plurality of time-varying acoustic parameters is modulated in accordance with at least the signal value of the time-domain signal.

(D)

622 — For a respective acoustic signal of the plurality of acoustic signals, generating the plurality of acoustic parameters includes generating a vowel-control parameter by:

624 — Selecting a sequence of acoustic waveform patterns from a set of N acoustic waveform patterns, the set of N acoustic waveform patterns arranged in a predefined order, where N is an integer greater than 2

626 — The sequence of acoustic waveform patterns includes a sequence of vowel waveform patterns 628 — Modulating a rate of selecting the sequence of acoustic waveform patterns in accordance with the signal value of the time-domain signal, to produce a signal-dependent rate of variation of acoustic waveform patterns 630 — Generating the vowel-control parameter corresponding to the signal-dependent rate of variation of acoustic waveform patterns (E)

Figure 6E

```
┌─────────────────────────────────────────────────────────────────┐
│ For each respective representation of an acoustic signal,       │
│ concurrently generate a plurality of acoustic parameters,       │
│ including a plurality of time-varying acoustic parameters.      │──612
│                                                                 │
│ One or more of the plurality of time-varying acoustic           │
│ parameters is modulated in accordance with at least the signal  │
│ value of the time-domain signal.                                │
│                                                                 │
│                            (E)                                  │
│   ┌─────────────────────────────────────────────────────────┐   │
│   │ For a respective acoustic signal of the plurality of    │──632
│   │ acoustic signals, generating the plurality of acoustic  │   │
│   │ parameters includes:                                    │   │
│   │  ┌───────────────────────────────────────────────────┐  │   │
│   │  │ Computing a time-varying amplitude value in       │──634
│   │  │ accordance with the signal value of the time-     │  │   │
│   │  │ domain signal                                     │  │   │
│   │  └───────────────────────────────────────────────────┘  │   │
│   │                           ▼                             │   │
│   │  ┌───────────────────────────────────────────────────┐  │   │
│   │  │ Generating a time-varying control parameter       │──636
│   │  │ corresponding to the computed time-varying        │  │   │
│   │  │ amplitude value                                   │  │   │
│   │  └───────────────────────────────────────────────────┘  │   │
│   │  ┌───────────────────────────────────────────────────┐  │   │
│   │  │           Selecting a base frequency              │──638
│   │  │   ┌─────────────────────────────────────────┐     │  │   │
│   │  │   │ The base frequency for each respective  │     │  │   │
│   │  │   │ acoustic signal is audibly distinct     │     │  │   │
│   │  │   │ from the base frequency of any other    │     │  │   │
│   │  │   │ acoustic signal of the plurality of     │     │  │   │
│   │  │   │ acoustic signals                        │──640 │  │   │
│   │  │   └─────────────────────────────────────────┘     │  │   │
│   │  └───────────────────────────────────────────────────┘  │   │
│   │                           ▼                             │   │
│   │  ┌───────────────────────────────────────────────────┐  │   │
│   │  │ Generating a time-varying pitch-control parameter │──642
│   │  │ in accordance with the selected base frequency    │  │   │
│   │  │ and the signal value of the time-domain signal    │  │   │
│   │  └───────────────────────────────────────────────────┘  │   │
│   │  ┌───────────────────────────────────────────────────┐  │   │
│   │  │ Selecting a sonic identity in accordance with a   │──644
│   │  │ spatial location, with respect to the subject's   │  │   │
│   │  │ body, of a sensor for sensing the time-domain     │  │   │
│   │  │ signal                                            │  │   │
│   │  └───────────────────────────────────────────────────┘  │   │
│   │                           ▼                             │   │
│   │  ┌───────────────────────────────────────────────────┐  │   │
│   │  │ Generating an identity-control parameter in       │──646
│   │  │ accordance with the selected sonic identity       │  │   │
│   │  └───────────────────────────────────────────────────┘  │   │
│   └─────────────────────────────────────────────────────────┘   │
└─────────────────────────────────────────────────────────────────┘
```

Figure 6F

SYSTEMS AND METHODS FOR PROCESSING SONIFIED BRAIN SIGNALS

CROSS-REFERENCE

N/A

BACKGROUND

The disclosed embodiments relate generally to the field of detecting signals from a living subject (e.g., electrical signals indicative of brain activity and/or heart activity), and in particular, to a system and method of sonifying signals from a living subject.

The ability to measure signals from a living subject (e.g., relating to the living subject's bodily functions) is beneficial for medical and diagnostic applications as well as for scientific research. For example, from a diagnostic point of view, measuring brain signals helps to ascertain brain activity related to abnormal brain function, to monitor spatial and/or temporal progression of brain disease, to aid surgical or nonsurgical intervention by localizing disease-sites in the brain, and to monitor brain activity of a healthy subject or a subject of unknown health status when the subject experiences a variety of stimuli and lack of stimuli. Likewise, measuring heart signals helps to diagnose both chronic and acute cardiac arrhythmias, other deficits in cardiac function, and potentially to monitor heart activity of a healthy subject or a subject of unknown health status when the subject experiences a variety of stimuli and lack of stimuli. From a scientific perspective, the ability to measure and study signals from a living subject (e.g., a human subject) facilitates scientific research aimed at understanding the structure and function of the human body.

SUMMARY

Traditional methods of measuring and analyzing signals from a living subject have not focused on sonification (e.g., aural presentation) of the signals. Moreover, applications beyond diagnostics and scientific research (e.g., applications in entertainment, therapy, etc.) have been largely neglected.

Accordingly, some embodiments provide a system and method for sonifying electrical signals obtained from a living subject. The method includes obtaining one or more time-domain signals, including at least one time-domain signal representing brain activity or heart activity. Each of the one or more time-domain signals has a time-varying signal value. The method further includes producing representations of a plurality of acoustic signals. Each representation of an acoustic signal of the plurality of acoustic signals corresponds to a respective time-domain signal of the one or more time-domain signals. Moreover, each representation of an acoustic signal of the plurality of acoustic signals is produced by concurrently generating a plurality of acoustic parameters, including a plurality of time-varying acoustic parameters. One or more of the plurality of time-varying acoustic parameters is modulated in accordance with at least the signal value of the respective time-domain signal. Each representation of an acoustic signal of the plurality of acoustic signals is further produced by combining the concurrently generated plurality of acoustic parameters to produce the representation of the acoustic signal corresponding to the respective time-domain signal. The method further includes combining the representations of each of the plurality of acoustic signals to produce a combined acoustic signal.

In another aspect, a method of sonifying signals obtained from a living subject is provided. The method includes obtaining a first time-domain electrical signal representing a first bodily function of the subject and a second time-domain electrical signal representing a second bodily function of the subject. The second bodily function is anatomically distinct from the first bodily function. The method further includes producing representations of a plurality of acoustic signals. Each representation of an acoustic signal of the plurality of acoustic signals corresponds to a time-domain signal. Moreover, each representation of an acoustic signal of the plurality of acoustic signals is produced by concurrently generating a plurality of acoustic parameters, including a plurality of time-varying acoustic parameters. One or more of the plurality of time-varying acoustic parameters is modulated in accordance with at least the signal value of the time-domain signal. Each representation of an acoustic signal of the plurality of acoustic signals is further produced by combining the concurrently generated plurality of acoustic parameters to produce the representation of the acoustic signal corresponding to the respective time-domain signal. The method further includes combining the representations of each of the plurality of acoustic signals to produce a combined acoustic signal.

In accordance with some embodiments, a computer system (e.g., a client system or server system) includes one or more processors, memory, and one or more programs; the one or more programs are stored in memory and configured to be executed by the one or more processors and the one or more programs include instructions for performing the operations of the method described above. In accordance with some embodiments, a non-transitory computer readable storage medium has stored therein instructions which when executed by one or more processors, cause a computer system (e.g., a client system or server system) to perform the operations of the methods described above.

Aspects of the present disclosure provide methods of sonifying electrical signals obtained from a living subject. In an exemplary method, a time-domain signal representing activity of an organ of the living subject may be obtained, a voltage of the time-domain signal over a time block may be determined, an acoustic signal based on the time-domain signal over the time block may be produced, and, if the determined voltage is over a threshold voltage, the time-domain signal may be squelched over at least a portion of the time-block as the acoustic signal is produced from the time-domain signal. The acoustic signal may comprise one or more audibly discernible variations representative of activity of the organ of the living subject. The acoustic signal may be musical. The time-domain signal may comprise one or more of an ECG, EKC, EEG, ENG, or EMG signal. The organ of the living subject may comprise a heart of the living subject, and the one or more audibly discernible variations may be representative of activity of the heart. Alternatively or in combination, the organ of the living subject may comprise a brain of the living subject, and the one or more audibly discernible variations may be representative of activity of the brain.

The acoustic signal may be audibly provided, with one or more speakers, to the living subject for feedback therapy for the living subject or to a living person other than the living subject for determining activity of the organ of the living subject. The feedback therapy or the determination of the activity of the organ may be based on the one or more audibly discernible variations.

The method may further comprise high-pass filtering a raw signal from the organ of the living subject to produce the time-domain signal.

The voltage of the time-domain signal over the time block may be determined by determining a root mean square (RMS) of the time-domain signal over the time block. The RMS of the time-domain signal may be determined after the time-domain signal has been fully acquired over the time block.

The time-domain signal may be squelched by ramping down the time-domain signal as an input to produce the acoustic signal. As the squelching is deactivated, the time-domain signal may be ramped back up as an input to produce the acoustic signal. The acoustic signal may be produced by combining the time-domain signal and a baseline signal. The time-domain signal may be squelched after the time-domain signal has been fully acquired over the time block.

Aspects of the present disclosure provide systems for sonifying electrical signals obtained from a living subject. An exemplary system may comprise one or more processors and a memory coupled to the one or more processors. The memory may comprise instructions for the one or more processors to: obtain a time-domain signal representing activity of an organ of the living subject, determine a voltage of the time-domain signal over a time block, produce an acoustic signal based on the time-domain signal over the time block, and squelch the time-domain signal over at least a portion of the time-block as the acoustic signal is produced from the time-domain signal if the determined voltage is over a threshold voltage. The acoustic signal may comprise one or more audibly discernible variations representative of activity of the organ of the living subject. The acoustic signal may be musical. The time-domain signal may comprise one or more of an ECG, EKC, EEG, ENG, or EMG signal. The organ of the living subject may comprise a heart of the living subject, and the one or more audibly discernible variations may be representative of activity of the heart. Alternatively or in combination, the organ of the living subject may comprise a brain of the living subject, and the one or more audibly discernible variations may be representative of activity of the brain.

The system may further comprise one or more speakers. The instructions of the memory further instructs the one or more processors to audibly provide, with the one or more speakers, the acoustic signal to the living subject for feedback therapy for the living subject or to a living person other than the living subject for determining activity of the organ of the living subject. The feedback therapy or the determination of the activity of the organ may be based on the one or more audibly discernible variations.

The instructions of the memory may further instruct the one or more processors to high-pass filter a raw signal from the organ of the living subject to produce the time-domain signal.

The instructions of the memory may further instruct the one or more processors to determine the voltage of the time-domain signal over the time block by determining a root mean square (RMS) of the time-domain signal over the time block. The RMS of the time-domain signal may be determined after the time-domain signal has been fully acquired over the time block.

The instructions of the memory may further instruct the one or more processors to squelch the time-domain signal by ramping down the time-domain signal as an input to produce the acoustic signal. The instructions of the memory may further instruct the one or more processors to ramp back up the time-domain signal as the input to produce the acoustic signal, as the squelching is deactivated. The acoustic signal may be produced by combining the time-domain signal and a baseline signal. The time-domain signal may be squelched after the time-domain signal has been fully acquired over the time block.

Aspects of the present disclosure provide methods of sonifying electrical signals obtained from a living subject. In an exemplary method, a time-domain signal representing activity of an organ of the living subject may be obtained, an acoustic signal based on the time-domain signal may be produced, and a frequency spectrum of the acoustic signal being produced may be adjusted. The acoustic signal may comprise one or more audibly discernible variations representative of activity of the organ of the living subject. The acoustic signal may be musical. The time-domain signal may comprise one or more of an ECG, EKC, EEG, ENG, or EMG signal. The organ of the living subject may comprise a heart of the living subject, and the one or more audibly discernible variations may be representative of activity of the heart. The organ of the living subject may comprise a brain of the living subject, and the one or more audibly discernible variations may be representative of activity of the brain.

The method may further comprise audibly providing, with one or more speakers, the acoustic signal with the adjusted frequency spectrum to the living subject for feedback therapy for the living subject or to a living person other than the living subject for determining activity of the organ of the living subject. The feedback therapy or the determination of the activity of the organ may be based on the one or more audibly discernible variations. The frequency spectrum of the acoustic signal may be adjusted at least partially based on a frequency response of the one or more speakers.

The frequency spectrum of the acoustic signal may be adjusted by passing the acoustic signal through an equalization filter.

The frequency spectrum of the acoustic signal may be adjusted boosting low frequencies of the frequency spectrum of the acoustic signal. The low frequencies of the frequency spectrum may be in a range from about 100 to 600 Hz. The low frequencies of the frequency spectrum may be in a vocal range of humans.

The frequency spectrum of the acoustic signal may be adjusted by attenuating high frequencies of the frequency spectrum of the acoustic signal. The high frequencies of the frequency spectrum may be in a range from about 1,000 to 20,000 Hz. The high frequencies of the frequency spectrum may be in a vocal range of humans.

Aspects of the present disclosure provide systems for sonifying electrical signals obtained from a living subject. The system may comprise one or more processors and a memory coupled to the one or more processors. The memory may comprise instructions for the one or more processors to: obtain a time-domain signal representing activity of an organ of the living subject, produce an acoustic signal based on the time-domain signal, and adjust a frequency spectrum of the acoustic signal being produced. The acoustic signal may comprise one or more audibly discernible variations representative of activity of the organ of the living subject. The acoustic signal may be musical. The time-domain signal may comprise one or more of an ECG, EKC, EEG, ENG, or EMG signal. The organ of the living subject may comprise a heart of the living subject, and the one or more audibly discernible variations may be representative of activity of the heart. The organ of the living subject may comprise a brain of the living subject, and the one or more audibly discernible variations may be representative of activity of the brain.

The system may further comprise one or more speakers. The instructions of the memory may further instruct the one or more processors to audibly provide, with the one or more speakers, the acoustic signal to the living subject for feedback therapy for the living subject or to a living person other than the living subject for determining activity of the organ of the living subject. The feedback therapy or the determination of the activity of the organ may be based on the one or more audibly discernible variations.

The instructions of the memory may further instruct the one or more processors to adjust the frequency spectrum of the acoustic signal by passing the acoustic signal through an equalization filter.

The instructions of the memory may further instruct the one or more processors to adjust the frequency spectrum of the acoustic signal by boosting low frequencies of the frequency spectrum of the acoustic signal. The low frequencies of the frequency spectrum may be in a range from about 100 to 600 Hz. The low frequencies of the frequency spectrum may be in a vocal range of humans.

The instructions of the memory may further instruct the one or more processors to adjust the frequency spectrum of the acoustic signal by attenuating high frequencies of the frequency spectrum of the acoustic signal. The high frequencies of the frequency spectrum may be in a range from about 1,000 to 20,000 Hz. The high frequencies of the frequency spectrum may be in a vocal range of humans.

Aspects of the present disclosure provide methods of sonifying electrical signals obtained from a living subject. In an exemplary method, a time-domain signal representing activity of a target organ of the living subject may be obtained, a measurement acoustic signal based on the time-domain signal may be produced, and a comparison acoustic signal may be provided. The measurement acoustic signal may comprise one or more audibly discernible variations representative of activity of the target organ of the living subject. The comparison acoustic signal may comprise one or more audibly discernible variations representative of comparable activity of the target organ of a sample subject. The time-domain signal may comprise one or more of an ECG, EKC, EEG, ENG, or EMG signal. The target organs of the living subject and the sample subject may each comprise a heart, and the one or more audibly discernible variations of the measurement acoustic signal and the comparison acoustic signal may be representative of activity of the heart. The target organs of the living subject and the sample subject may each comprise a brain, and the one or more audibly discernible variations of the measurement acoustic signal and the comparison acoustic signal may be representative of activity of the brain.

The measurement acoustic signal may be audibly provided, with one or more speakers, to the living subject for feedback therapy for the living subject or to a living person other than the living subject for determining activity of the target organ of the living subject. The feedback therapy or the determination of the activity of the target organ may be based on the one or more audibly discernible variations of the measurement acoustic signal.

The comparison acoustic signal may be audibly provided, with one or more speakers, for determining activity of the target organ of the living subject. The activity of the target organ may be determined by comparing the measurement acoustic signal with the comparison acoustic signal.

The comparison acoustic signal may be provided by providing a database or library of a plurality of comparison acoustic signals.

Aspects of the present disclosure provide systems for sonifying electrical signals obtained from a living subject. An exemplary system may comprise one or more processors and a memory coupled to the one or more processors. The memory may comprise instructions for the one or more processors to: obtain a time-domain signal representing activity of a target organ of the living subject, produce a measurement acoustic signal based on the time-domain signal, and provide a comparison acoustic signal. The measurement acoustic signal may comprise one or more audibly discernible variations representative of activity of the target organ of the living subject. The comparison acoustic signal may comprise one or more audibly discernible variations representative of comparable activity of the target organ of a sample subject. The time-domain signal may comprise one or more of an ECG, EKC, EEG, ENG, or EMG signal. The target organs of the living subject and the sample subject may each comprise a heart, and the one or more audibly discernible variations of the measurement acoustic signal and the comparison acoustic signal may be representative of activity of the heart. The target organs of the living subject and the sample subject may each comprise a brain, and the one or more audibly discernible variations of the measurement acoustic signal and the comparison acoustic signal may be representative of activity of the brain.

The system may further comprise one or more speakers. The one or more processors may be configured to instruct the one or more speakers to audibly provide the measurement acoustic signal to the living subject for feedback therapy for the living subject or to a living person other than the living subject for determining activity of the target organ of the living subject. The feedback therapy or the determination of the activity of the target organ may be based on the one or more audibly discernible variations of the measurement acoustic signal.

The one or more processors may be further configured to instruct the one or more speakers to audibly provide the comparison acoustic signal for determining activity of the target organ of the living subject. The activity of the target organ may be determined by comparing the measurement acoustic signal with the comparison acoustic signal.

The system may further comprise a database or library of a plurality of comparison acoustic signals. This database or library may be stored in the memory of the system and/or be accessible from the system as a remote database.

Aspects of the present disclosure provide methods of sonifying electrical signals obtained from a living subject. In an exemplary method, a time-domain signal representing activity of an organ of the living subject may be obtained, an acoustic signal may be produced based on the time-domain signal over a time block, and the acoustic signal may be stored, and one or more data tags may be appended to the stored acoustic signal. The acoustic signal may comprise one or more audibly discernible variations representative of activity of the organ of the living subject. The acoustic signal may be musical. The time-domain signal may comprise one or more of an ECG, EKC, EEG, ENG, or EMG signal. The organ of the living subject may comprise a heart of the living subject, and the one or more audibly discernible variations may be representative of activity of the heart. The organ of the living subject may comprise a brain of the living subject, and the one or more audibly discernible variations may be representative of activity of the brain.

The acoustic signal may be audibly provided, with one or more speakers, to the living subject for feedback therapy for the living subject or to a living person other than the living subject for determining activity of the organ of the living subject. The feedback therapy or the determination of the activity of the organ may be based on the one or more audibly discernible variations.

The one or more data tags may be appended to the stored acoustic signal by providing a user interface for a user to input the one or more data tags. The one or more data tags may be input by the user in response to the user listening to the acoustic signal. The one or more data tags may contain a timestamp. The one or more tags may indicate a physiological event related to the activity of the organ of the living subject. The one or more tags may be automatically generated, and the one or more data tags may be automatically appended.

Aspects of the present disclosure may provide systems for sonifying electrical signals obtained from a living subject. An exemplary system may comprise one or more processors and a memory coupled to the one or more processors. The memory may comprise instructions for the one or more processors to: obtain a time-domain signal representing activity of an organ of the living subject, produce an acoustic signal based on the time-domain signal over the time block, store the acoustic signal, and append one or more data tags to the stored acoustic signal. The acoustic signal may comprise one or more audibly discernible variations representative of activity of the organ of the living subject. The acoustic signal may be musical. The time-domain signal may comprise one or more of an ECG, EKC, EEG, ENG, or EMG signal. The organ of the living subject may comprise a heart of the living subject, and the one or more audibly discernible variations are representative of activity of the heart. The organ of the living subject may comprise a brain of the living subject, and the one or more audibly discernible variations may be representative of activity of the brain.

The system may further comprise one or more speakers. The instructions of the memory may further instruct the one or more processors to audibly provide, with the one or more speakers, the acoustic signal to the living subject for feedback therapy for the living subject or to a living person other than the living subject for determining activity of the organ of the living subject. The feedback therapy or the determination of the activity of the organ may be based on the one or more audibly discernible variations.

The system may further comprise a user interface, and the one or more data tags may be appended to the stored acoustic signal by providing the user interface for a user to input the one or more data tags. The one or more data tags may be input by the user in response to the user listening to the acoustic signal. The one or more data tags may contain a timestamp. The one or more tags may indicate a physiological event related to the activity of the organ of the living subject. The one or more tags may be automatically generated, and the one or more data tags may be automatically appended.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

FIGS. 6A-6F include flow charts illustrating methods for sonifying signals obtained from a living subject, in accordance with some embodiments.

DETAILED DESCRIPTION

Figure 1:
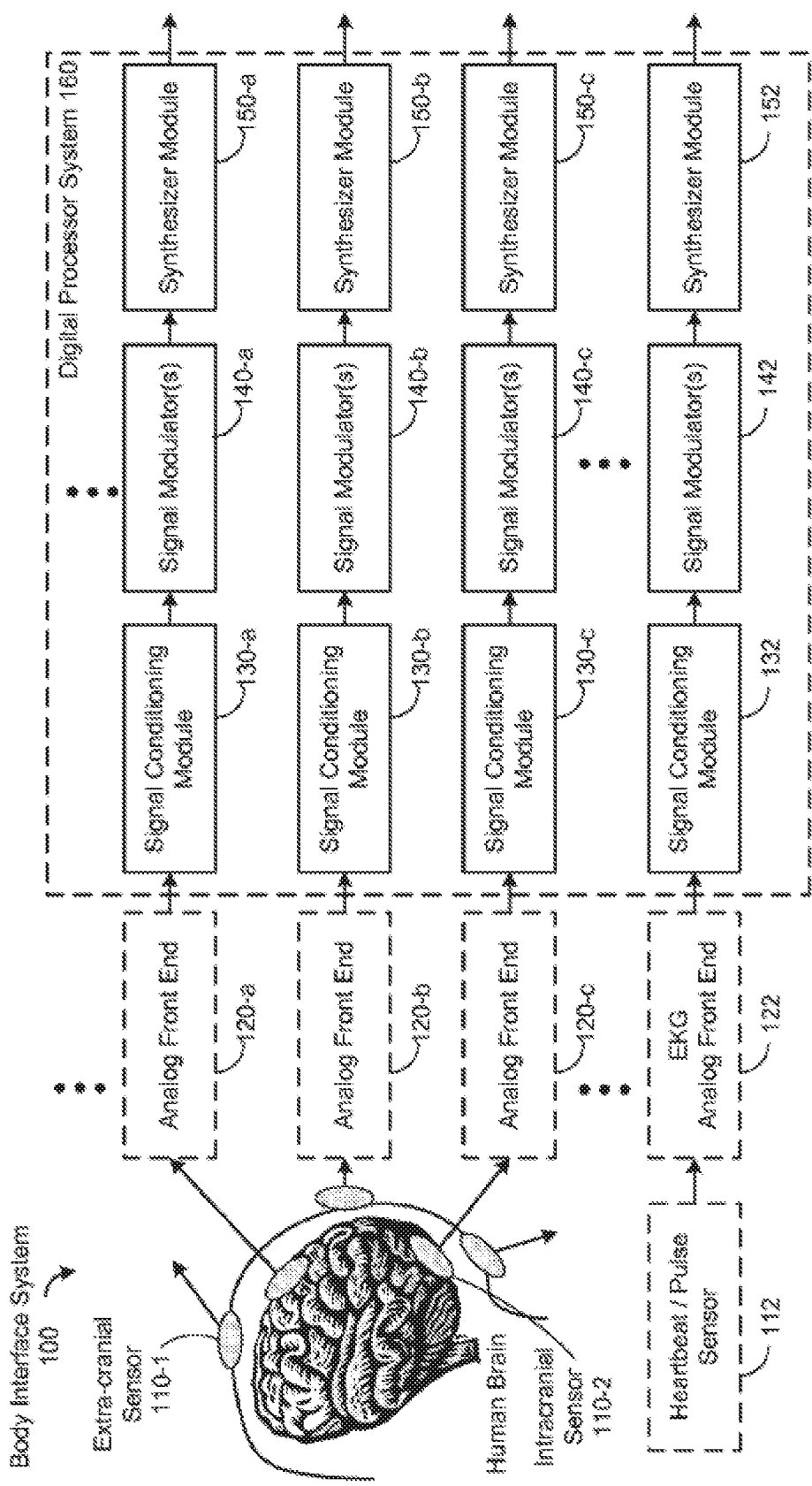
FIG. 1 illustrates a body interface system for acquiring and processing signals from a living subject, in accordance with some embodiments.

Traditional approaches to measuring signals from a living subject (e.g., location-specific brain signals, or electrocardiography (ECG) signals corresponding to heart activity) typically involve recording and visually displaying electrical signals acquired from the brain or other organs. Moreover, these approaches are typically used for diagnostic or scientific purposes. When represented in visual or graphical form, subtle features and attributes—and subtle changes in features and attributes—of the electrical signals may not be easily discernible. However, when sonified or converted to auditory form, these subtle features and attributes can become more apparent. Furthermore, sonification methodologies that transform the signals acquired from the living subject into vocal patterns and vocal parameters—and changes in vocal patterns and vocal parameters—that resemble a human voice make it easier to discern, upon auditory inspection, subtleties in the underlying electrical signals that correspond to bodily function.

Additionally, traditional approaches to measuring signals from a living subject have not focused on applications beyond diagnostics and scientific research. To that end, a method of sonifying signals obtained from a living subject is provided. In particular, in some embodiments, the method transforms signals acquired from the living subject into vocal patterns and vocal parameters that can be used for applications in entertainment as well as user interfaces for electronic devices.

The method includes obtaining a first time-domain electrical signal representing a first bodily function of the subject and a second time-domain electrical signal representing a second bodily function of the subject, the second bodily function being anatomically distinct from the first bodily function (e.g., the first bodily function and the second bodily function correspond to distinct bodily organs, such as the brain, heart, or a muscle, or organ systems, such as the circulatory system, muscular system, or nervous system). In some embodiments, the first time-domain electrical signal and/or the second time-domain electrical signal measure a metric associated with a non-electrical bodily function that is converted to an electrical signal by a measurement apparatus. For example, in some embodiments, the first time-domain electrical signal and/or the second time-domain electrical signal is one of a pulse oximetry signal, a capnography signal, a photoplethysmography signal, or the like. Alternatively, the first time-domain electrical signal and/or the second time-domain electrical signal measure an electrical activity of the body (e.g., using electrodes). For example, in some embodiments, the first time-domain electrical signal and/or the second time-domain electrical signal measure an electrocardiography (ECG) signal, an electroencephalography (EEG) signal, an electromyography (EMG) signal, an electronystagmography (ENG) signal, or the like.

The method includes producing representations of a plurality of acoustic signals. Each representation of an acoustic signal of the plurality of acoustic signals corresponds to a time-domain signal and is produced by concurrently generating a plurality of acoustic parameters, including a plurality of time-varying acoustic parameters. One or more of the plurality of time-varying acoustic parameters is modulated in accordance with at least the signal value of the time-domain signal. Each representation of an acoustic signal of the plurality of acoustic signals is further produced by combining the concurrently generated plurality of acoustic parameters to produce the representation of the acoustic signal corresponding to the respective time-domain signal.

In some implementations, the method further includes combining the representations of each of the plurality of acoustic signals to produce a combined acoustic signal. In some other implementations, two or more of the representations of the acoustic signals are recorded on separate tracks, or directed to distinct speakers, for concurrent production as acoustic signals. As a result, a combined acoustic signal, corresponding to representations of the plurality of acoustic signals, is generated (e.g., generated "in the air") by concurrent production of two or more individual acoustic signals within a physical space or in a manner that enables the concurrently produced acoustic signals to be heard concurrently by a human listener.

For example, some embodiments described below combine sonified signals from the living subject's heart with signals from the living subject's brain to produce a combined acoustic signal. The combined acoustic signal, in audible form, manifests one or more audibly discernible variations of the living subject's response to an external stimulus (e.g., visual, and/or aural). For example, in some embodiments, the external stimulus includes music (to which the living subject is listening), a video game (e.g., a video game played by the living subject or watched by the living subject), a physical game (e.g., a video game played by the living subject or watched by the living subject), and/or exercise, and the combined acoustic signal is provided to the subject as a custom soundtrack. In some embodiments, the combined acoustic signal is aurally provided to the living subject in real-time as biofeedback, for example as a neurofeedback for neurotherapy (e.g., the combined acoustic signal comprises a hemoencephalography (HEG) feedback signal). In some embodiments, the neurotherapy comprises a therapy for at least one of: migraines, autism, attention deficit hyperactivity disorder (ADHD), and/or cognitive performance.

In some implementations, the combined acoustic signal produced by performance of any of the sonification methods described herein is provided to a living person (sometimes called the second person for ease of reference) other than the living subject (sometimes called the first person for ease of reference) whose brain activity, heart activity, and/or other bodily functions are monitored and sonified using any of the sonification methods described herein. For example, the second person listens to the combined acoustic signal of the first person while the first person performs an activity, such as listening to music, conversing with the second person, playing or watching a video game, playing or watching a physical game, exercising, reading a document, engaging in a particular mental activity such as solving a problem or puzzle, counting backwards, detecting a pattern in information presented visually and/or audibly, etc. In some implementations, the sonification method described herein is performed, independently, on first and second living subjects, producing first and second combined acoustic signals corresponding to the first and second living subjects, respectively, and providing the first combined acoustic signal to the second living subject and providing the second combined acoustic signal to the first living subject. In some implementations, any of the aforementioned methods are performed while monitoring only brain activity of the living subject (or both living subjects), or while monitoring only one bodily function (e.g., monitoring a heart activity signal or any other bodily function signals) of the living subject (or both living subjects).

In some embodiments, the sonification methodologies described herein are encoded within instructions that comprise an application (e.g., an "app") on a portable multi-function device (e.g., an exercise app or a gaming app). In some embodiments, the application interfaces with one or more dry-sensors (e.g., conductive sensors that are mechanically placed against a living subject's body rather implanted within the living subject's body or held in place with a sticky conductive gel).

Reference will now be made in detail to various embodiments, examples of which are illustrated in the accompanying drawings. In the following detailed description, numerous specific details are set forth in order to provide a thorough understanding of the invention and the described embodiments. However, the invention is optionally practiced without these specific details. In other instances, well-known methods, procedures, components, and circuits have not been described in detail so as not to unnecessarily obscure aspects of the embodiments.

It will be understood that, although the terms "first," "second," etc. are optionally used herein to describe various elements, these elements should not be limited by these terms. These terms are only used to distinguish one element from another. For example, a first sensor could be termed a second sensor, and, similarly, a second sensor could be termed a first sensor, without changing the meaning of the description, so long as all occurrences of the "first sensor" are renamed consistently and all occurrences of the second sensor are renamed consistently. The first sensor and the second sensor are both sensors, but they are not the same sensor.

The terminology used herein is for the purpose of describing particular embodiments only and is not intended to be limiting of the claims. As used in the description of the embodiments and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" is optionally construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" is optionally construed to mean "upon determining" or "in response to determining" or "in accordance with a determination" or "upon detecting" or "in response to detecting" that the stated condition precedent is true, depending on the context.

For ease of explanation, FIGS. 1-3B are described below with reference to sonification of signals representing brain activity (e.g., electroencephalography (EEG) signals) and/or heart activity (e.g., electrocardiography (ECG) signals) of a living subject. However, one of skill in the art will recognize that signals representing other bodily functions (e.g., an electromyography (EMG) signal, or an electronystagmography (ENG) signal, a pulse oximetry signal, a capnography signal, and/or a photoplethysmography signal) may be substituted, or used in addition to (e.g., in conjunction with), one or more signals representing brain activity and/or heart activity.

FIG. 1 illustrates body interface system 100 for sensing, acquiring and processing one or more signals (typically two or more signals) obtained from a living subject (e.g., obtained from a human's brain and/or heart) to produce a representation of an acoustic signal corresponding to the one or more (or two or more) signals (e.g., representing brain and/or heart activity). In some circumstances, body interface system 100 is deployed in a clinical setting (e.g., during or before surgical interventions and/or during diagnosis and/or treatment of conditions, such as epileptic seizures) for aural (e.g., auditory) measurement or monitoring of brain activity. Alternatively, or in addition, body interface system 100 is deployed as part of a user interface for a portable electronic device (e.g., a smart-phone, tablet, or the like) for entertainment, biofeedback, monitoring, therapeutic or other purposes.

In some embodiments, as shown in FIG. 1, body interface system 100 includes one or more sensor(s) 110, optionally includes one or more analog front end(s) 120 (e.g., one or more analog front end modules), one or more electrocardiography (ECG) analog front end(s) 122, and a digital processor system 160 (herein often called digital processor 160 for ease of reference). In some other embodiments, analog front end 122 is an analog front end for a sensor other than a heartbeat or pulse sensor.

In some embodiments, sensor(s) 110 are provided to interface with a living subject's brain to obtain (e.g., sense and/or acquire) sensor time-domain signals (e.g., sensor time-domain signal 201, FIG. 2A) corresponding to brain electrical activity. For example, signals (e.g., sensor time-domain signal 201, FIG. 2A) corresponding to brain electrical activity are obtained from a human brain and correspond to electrical signals obtained from a single neuron or from a plurality of neurons. In some embodiments, sensor(s) 110 include(s) one or more sensors affixed (e.g., taped, attached, glued) externally to a human scalp (e.g., extra-cranial sensor 110-1). For example, extra-cranial sensor 110-1 include(s) an electrode (e.g., electroencephalography (EEG) electrode) or a plurality of electrodes (e.g., electroencephalography (EEG) electrodes) affixed externally to the scalp (e.g., glued to the skin via conductive gel), or more generally positioned at respective positions external to the scalp. Alternatively, dry electrodes can be used in some implementations (e.g., conductive sensors that are mechanically placed against a living subject's body rather than being implanted within the living subject's body or held in place with a conductive gel). An example of a dry electrode is a headband with one or more metallic sensors (e.g., electrodes) that is worn by the living subject during use. The signals obtained from an extra-cranial sensor 110-1 are sometimes herein called EEG signals or time-domain EEG signals.

In some embodiments, sensor(s) 110 include(s) a sensor embedded in a particular location of a brain (e.g., intracranial sensor 110-2). For example, intracranial sensor 110-2 is formed (e.g., fabricated) on a needle embedded in a particular location of the brain with one or more sensing elements located along the length and/or circumference of the needle. In some embodiments, a plurality of sensor(s) 110 (e.g., intracranial sensor 110-2) is formed (e.g., fabricated) on a single needle (e.g., 8 instances of sensor(s) 110 or 8 sensing elements are formed on a single needle) embedded in a particular location of a brain. In some embodiments, intracranial sensor 110-2 includes intracranial depth electrodes implanted in the brain at a plurality of locations to monitor electrical activity in the brain at the plurality of locations. In some embodiments, a plurality of sensor(s) 110 (e.g., numbering between 4 and 80 sensors) is embedded across a plurality of regions of interest in the brain. In such embodiments, individual sensors are sensitive to small electrical potential changes caused by neural signaling at corresponding locations in the brain (or in corresponding regions of the brain). In some implementations, the observed signal (e.g., sensor time-domain signal 201, FIG. 2A) obtained from each sensor 110 (e.g., intracranial sensor 110-2) represents the aggregate activity (e.g., corresponding to 10,000 neurons) in a region proximal to the respective sensor (e.g., intracranial sensor 110-2).

In some embodiments, heartbeat pulse sensor(s) 112 are provided to interface with a living subject's heart to obtain (e.g., sense and/or acquire) sensor time-domain signals (e.g., sensor time-domain signal 201, FIG. 2A) corresponding to heart electrical activity. For example, signals (e.g., sensor time-domain signal 201, FIG. 2A) corresponding to heart electrical activity are obtained from a human heart and correspond to electrical signals obtained from a single cardiomyocyte or from a plurality of cardiomyocytes (e.g., a sinoatrial (SA) node of a human subject). In some embodiments, heartbeat pulse sensor(s) 112 include(s) one or more sensing elements affixed (e.g., taped, attached, glued) externally to a human body (e.g., a human subject's chest, abdomen, arm, or leg). For example, heartbeat pulse sensor(s) 112 include(s) an electrode (e.g., electrocardiography (ECG) electrode) or a plurality of electrodes (e.g., electrocardiography (ECG) electrodes) affixed externally to the human body (e.g., glued to the skin via conductive gel), or more generally positioned at respective positions external to the human body. Alternatively, dry electrodes can be used in some implementations (e.g., conductive sensors that are mechanically placed against a human body rather than being implanted within the human body or held in place with a conductive gel). An example of a dry electrode is a chest strap with one or more metallic sensors (e.g., electrodes) that is worn by the living subject during use. Another example of a dry electrode is a thumb apparatus or a hand apparatus with one or more metallic sensing elements (e.g., electrodes) that is touched (e.g., with the living subject's thumbs) and/or held onto (e.g., with the living subject's hands) by the living subject during use. The signals obtained from heartbeat pulse sensor(s) 112 are sometimes herein called ECG signals or time-domain ECG signals.

In some embodiments, heartbeat pulse sensor(s) 112 sense voltages corresponding to heart electrical activity. In alternative embodiments, heartbeat pulse sensor(s) 112 sense electrical currents corresponding to heart electrical activity. In some implementations, heartbeat pulse sensor(s) 112 sense differential voltages (e.g., differences in voltage values) between two measurement locations (e.g., between two sensing elements). For example, when a respective heartbeat pulse sensor 112 includes two or more sensing elements (e.g., electrodes) positioned at respective positions external to the human body, the respective heartbeat pulse sensor 112 senses differential voltages between the two or more sensing elements located at the respective positions. In some implementations, a "twelve-lead electrocardiogram" is constructed by referencing each sensing element of a set of sensing elements to one or more other sensing elements to produce a corresponding set of differential voltage signals (e.g., a twelve-lead set of differential voltage signals), each of which is a respective sensor time-domain signal 201, FIG. 2A.

Figure 2A:
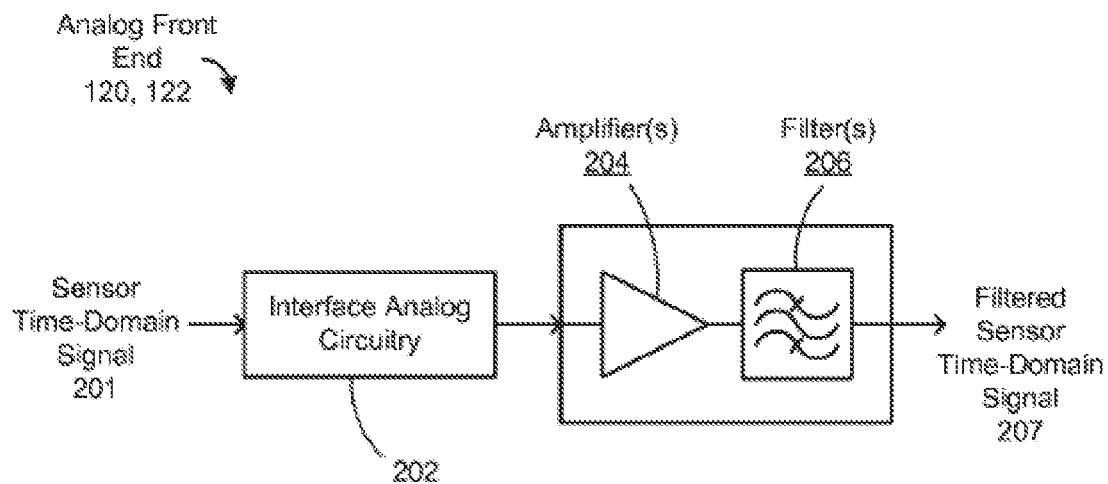
FIG. 2A is a block diagram illustrating an analog front end used for pre-processing electrical signals obtained from a living subject, in accordance with some embodiments.

In some embodiments, arrays of sensors (e.g., sensor(s) 110 and/or heartbeat pulse sensor(s) 112, herein sometimes referred to collectively as "sensor(s) 110/112") are designed to produce a plurality of sensor time-domain signals (e.g., sensor time-domain signals 201, FIG. 2A). In some embodiments, sensor time-domain signals (e.g., sensor time-domain signal 201, FIG. 2A) include wideband features including high-gamma bursts in the range of 80-150 Hz. In some embodiments, sensor(s) 110 embedded in a particular location of the brain are additionally configured to dispense medication to localized portions of the brain. In some embodiments, sensor time-domain signals (e.g., sensor time-domain signal 201, FIG. 2A) include frequencies (sometimes called frequency components) below (e.g., lower than or in the lowest ranges of) the human audible frequency-range.

In some implementations, analog front end 120 and/or electrocardiography (ECG) analog front end 122 (herein sometimes referred to collectively as "analog front end(s) 120/122") receives sensor time-domain signals (e.g., sensor time-domain signal 201, FIG. 2A) from sensor(s) 110/112 and optionally pre-processes the sensor time-domain signals to produce filtered sensor time-domain signals (e.g., filtered sensor time-domain signals 207, FIG. 2A). In some embodiments, a separate (e.g., independent) analog front end is provided for interfacing with each of a set of sensor(s) 110/112. In some embodiments, a first analog front end is provided for interfacing with a set of sensor(s) 110, and a second (i.e., distinct) electrocardiography (ECG) analog front end 122 is provided for interfacing with a set of heartbeat pulse sensor(s) 112. In such embodiments, body interface system 100 comprises a plurality of analog front end modules (e.g., analog front end 120-a, analog front end 120-b, analog front end 120-c, etc., and optionally one or more electrocardiography (ECG) analog front end(s) 122) for interfacing with a plurality of sensor(s) 110/112.

As shown in FIG. 1, body interface system 100 includes digital processor system 160 for processing signals obtained from the living subject (e.g., signals corresponding to electrical activity of the brain or heart), optionally after the signals are pre-processed by analog front end 120/122. Digital processor 160 includes signal conditioning module(s) 130/132, signal modulator(s) 140/142, and synthesizer module(s) 150/152. In some embodiments, a separate (e.g., independent) signal conditioning module, a separate (e.g., independent) signal modulator, and/or a separate (e.g., independent) synthesizer module is provided for interfacing with each sensor 110/112 in a set of two or more sensors 110/112 (optionally through a separate analog front end module). In such embodiments, body interface system 100 comprises a plurality of signal conditioning modules (e.g., signal conditioning module 130-a, signal conditioning module 130-b, signal conditioning module 130-c, etc., and optionally one or more signal conditioning module(s) 132), a plurality of signal modulator(s) (e.g., signal modulator(s) 140-a, signal modulator(s) 140-b, signal modulator(s) 140-c, etc., and optionally one or more signal modulator(s) 142), and/or a plurality of synthesizer modules (e.g., synthesizer module 150-a, synthesizer module 150-b, synthesizer module 150-c, etc., and optionally one or more synthesizer modules 152) for interfacing with a plurality of sensors 110/112 and processing signals obtained from those sensors.

In some embodiments, a respective signal conditioning module 130/132 includes a data convertor (e.g., an analog to digital convertor for converting an analog filtered sensor time-domain signal obtained from sensor(s) 110/112 to a corresponding digital representation), an upsampler and a digital low-pass filter. In some implementations, signal modulators 140/142 receive the digitized time-domain signals output by signal conditioning modules 130/132, and concurrently generate a set of acoustic parameters, including a plurality of time-varying acoustic parameters from (e.g., using) the digitized time-domain signals. One or more of the plurality of time-varying acoustic parameters is modulated in accordance with at least the signal value of the time-domain signal (e.g., time-domain signal 218, FIG. 2B, produced by signal conditioning module 130/132). In some embodiments, synthesizer module (e.g., synthesizer module 150/152) combines the concurrently generated set of acoustic parameters to produce a representation of an acoustic signal corresponding to the time-domain signal (e.g., time-domain signal 218, FIG. 2B, produced by signal conditioning module 130/132).

Figure 2B:
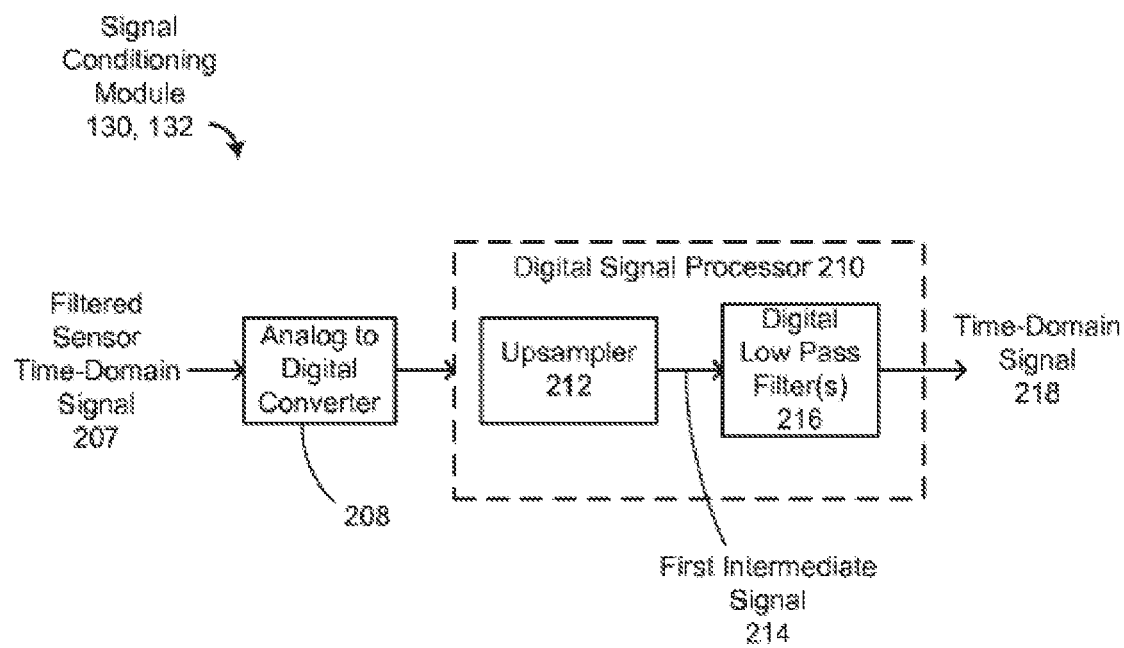
FIG. 2B is a block diagram illustrating a signal conditioning module used for processing electrical signals obtained from a living subject, in accordance with some embodiments.
Figure 2C:
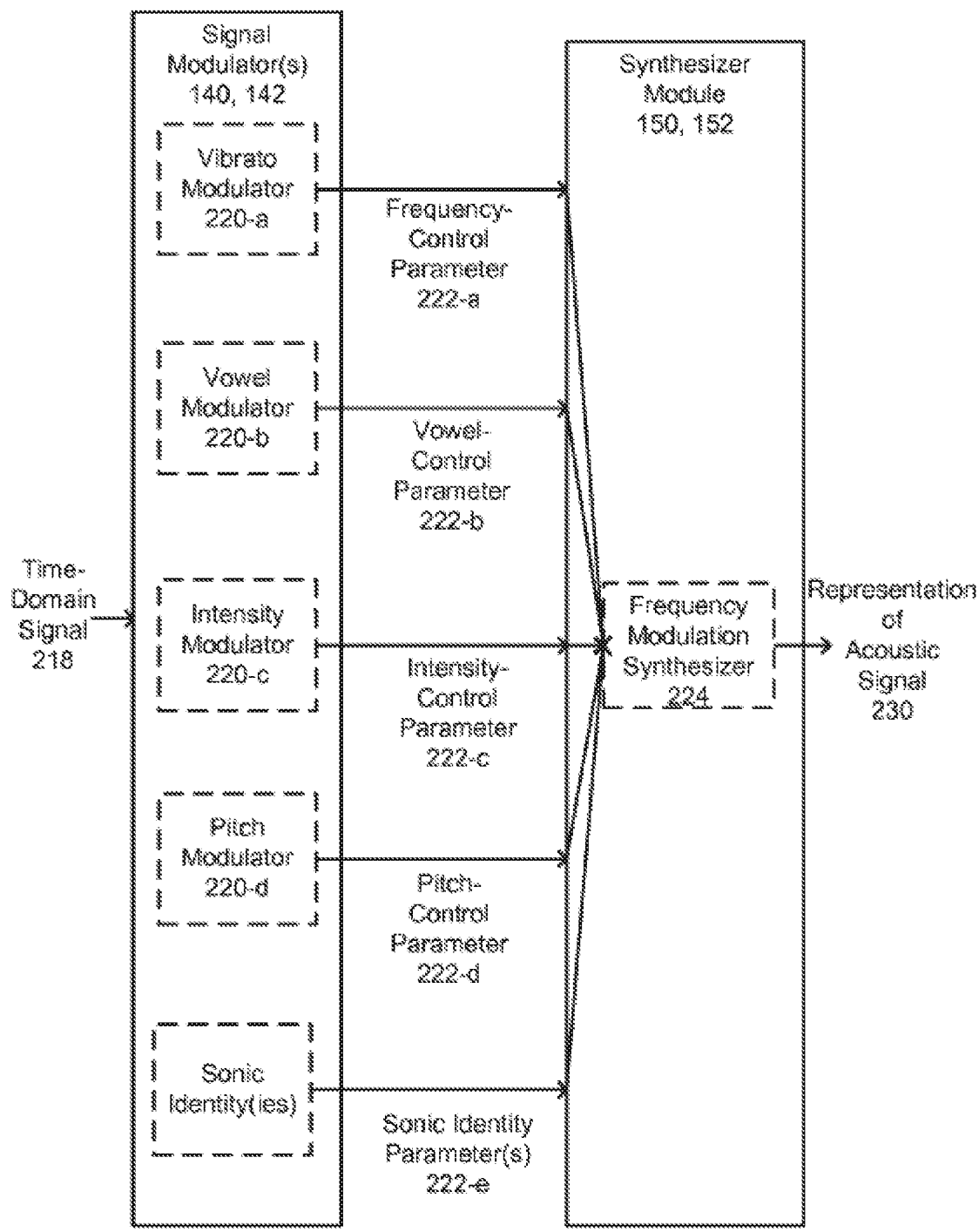
FIG. 2C is a block diagram illustrating signal modulators and a synthesizer module used for processing electrical time-domain signals obtained from a living subject to produce a representation of an acoustic signal, in accordance with some embodiments.
Figure 2D:
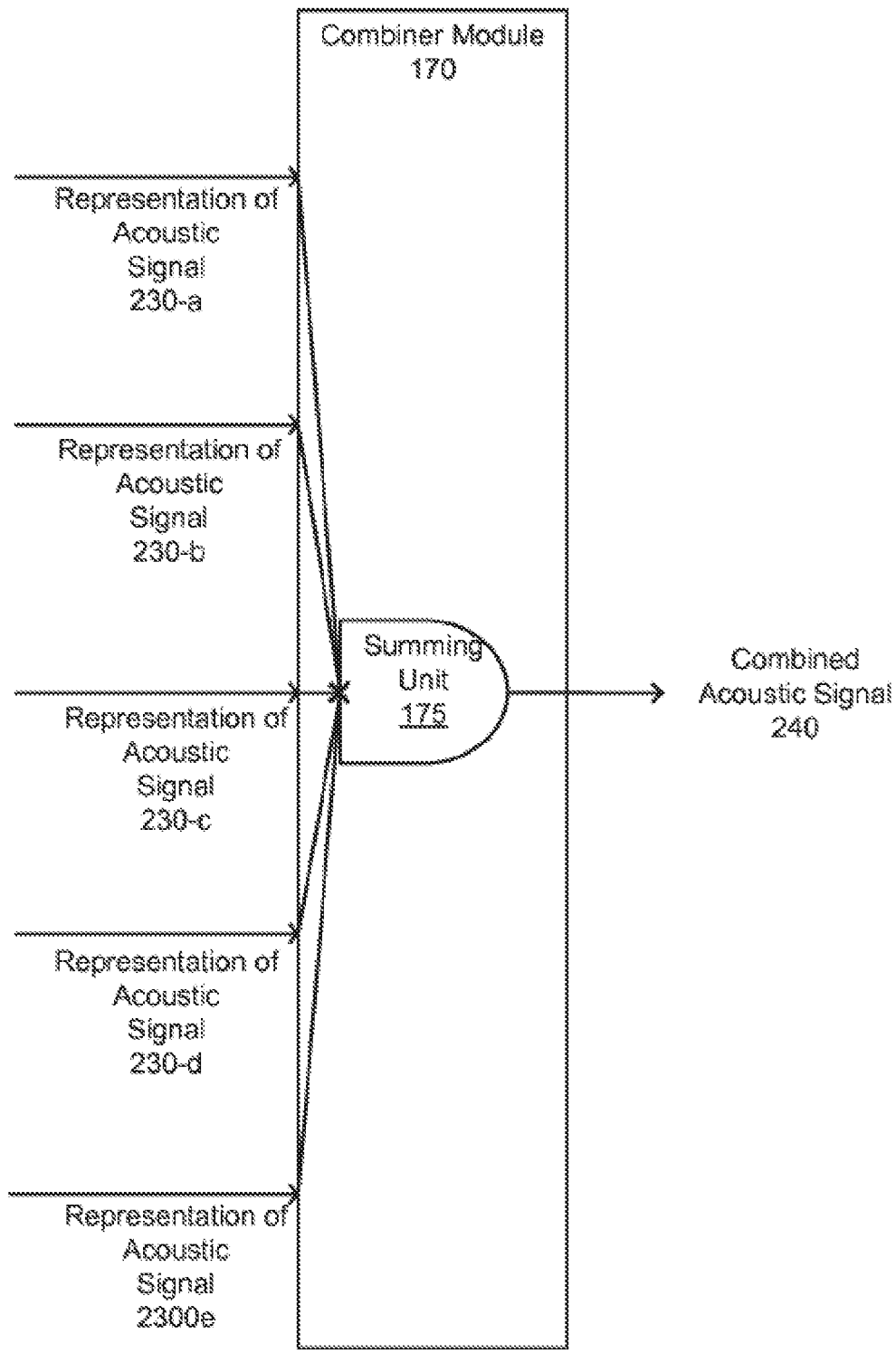
FIG. 2D is a block diagram of a combiner module used for combining a plurality of representations of acoustic signals, in accordance with some embodiments.

In some embodiments, a plurality of representations of acoustic signals are combined to produce a combined acoustic signal (e.g., combined acoustic signal 240, FIG. 2D). Alternatively, a combined acoustic signal is generated by combining acoustic signals corresponding to the plurality of representations of acoustic signals produced by digital processor system 160. In yet another alternative, a plurality of acoustic signals, each corresponding to one of more of the aforementioned representations of acoustic signals, are recorded on distinct tracks, where the distinct tracks are configured to enable concurrent playback of the acoustic signals recorded in those tracks.

FIG. 2A illustrates a block diagram of an analog front end (e.g., analog front end 120/122, FIG. 1) optionally included in body interface system 100. In some embodiments, analog front end 120/122 receives a sensor time-domain signal (e.g., sensor time-domain signal 201) from a respective sensor 110/112 and pre-processes the sensor time-domain signal to produce a filtered sensor time-domain signal (e.g., filtered sensor time-domain signal 207). When body interface system 100 includes a plurality of analog front ends 120/122, the analog front ends 120/122 process a corresponding number of sensor time-domain signals in parallel to produce filtered sensor time-domain signals.

In some embodiments, analog front end 120/122 includes interface circuitry (e.g., interface analog circuitry 202) to interface with a respective sensor 110/112, for example, by way of providing bias voltages and/or currents to the respective sensor 110/112, buffering signals (e.g., using a buffer amplifier) received from sensor(s) 110/112 and/or providing appropriate coupling conditions (e.g., providing appropriate input impedance) for interfacing with the signals received from sensor(s) 110/112.

Alternatively, or in addition, according to some implementations, analog front end 120/122 includes one or more amplifiers 204 and/or filters 206 to pre-process (e.g., amplify and/or filter) sensor time-domain signals corresponding to brain electrical activity or heart electrical activity (e.g., sensor time-domain signal 201, FIG. 2A) obtained (e.g., sensed and/or acquired) from one or more sensors 110/112. As noted above, in some embodiments, analog front end 120/122 produces a filtered sensor time-domain signal (e.g., filtered sensor time-domain signal 207).

FIG. 2B illustrates a block diagram of a signal conditioning module (e.g., signal conditioning module 130/132) included in body interface system 100. As shown in FIG. 2B, signal conditioning module 130/132 receives filtered sensor time-domain signals (e.g., filtered sensor time-domain signal 207)—optionally obtained after pre-processing by analog front end 120/122—and conditions the filtered sensor time-domain signals to produce time-domain signals (e.g., time-domain signal 218).

In some embodiments, the signal conditioning module (e.g., signal conditioning module 130/132) includes a data convertor (e.g., analog to digital convertor 208) for converting an analog filtered sensor time-domain signal obtained from sensor(s) 110/112 (optionally after pre-processing by analog front end 120/122) to a corresponding digital representation with a predefined sampling rate (e.g., a sampling rate between 500 Hz and 2 kHz, such as 500 Hz; or more generally a sampling rate between 400 Hz to 4 kHz). Signal conditioning module 130/132 includes an upsampler (e.g., upsampler 212) to upsample (e.g., increase the sampling rate of) the digital representation of the analog filtered sensor time-domain signal to produce a first intermediate signal (e.g., first intermediate signal 214). In some embodiments, the digital representation of the analog filtered sensor time-domain signal is upsampled to produce a first intermediate signal having an audio sampling rate, for example, a sampling rate (e.g., 48 kHz) used in conventional audio applications. In some implementations, the first intermediate signal (e.g., first intermediate signal 214) produced by upsampler 212 has a sampling rate of 48 kHz.

In some implementations, signal conditioning module 130/132 includes one or more digital low-pass filters (e.g., digital low pass filter(s) 216) for filtering first intermediate signal 214 so as to produce time-domain signal 218. In some implementations, digital low pass filter(s) 216 is a second order low-pass Butterworth filter with a 250 Hz corner frequency. Digital low pass filter(s) 216 filter(s) first intermediate signal 214 to produce time-domain signal 218. In some embodiments, upsampler 212 and digital low pass filter(s) 216 are implemented in digital signal processor 210, sometimes called a DSP. In some other implementations, upsampler 212 and digital low pass filter(s) 216 are implemented in circuitry. Alternatively, upsampler 212 and digital low pass filter(s) 216 are implemented in software executed by a general purpose processor. Without limitation, it is noted that upsampling and then low pass filtering the digital representation of the analog filtered sensor time-domain signal may be used to convert the output of one or more sensors (e.g., inter-cranial or extra-cranial sensors and/or heartbeat/pulse sensors) to a form that is suitable for use with a music or other audio synthesizer, while removing or limiting artifacts produces by the conversion process.

FIG. 2C illustrates a block diagram of signal modulators 140/142 and synthesizer module 150/152. Signal modulators 140/142 receive time-domain signal 218 from signal conditioning module 130/132 (as explained above with reference to FIG. 2B). Signal modulators 140/142 concurrently generate a set of acoustic parameters, including a plurality of time-varying acoustic parameters. In some embodiments, the plurality of acoustic parameters includes a frequency-control parameter (e.g., frequency-control parameter 222-a). In some embodiments, the plurality of acoustic parameters includes a vowel-control parameter (e.g., vowel-control parameter 222-b). In some embodiments, the plurality of acoustic parameters includes a time-varying intensity-control parameter (e.g., intensity-control parameter 222-c). In some embodiments, the set of acoustic parameters includes a pitch-control parameter (e.g., pitch-control parameter 222-

*d*). In some embodiments, the set of acoustic parameters includes one or more sonic identity parameters (e.g., sonic identity parameter(s) 222-*e*).

In some embodiments, signal modulator(s) 140/142 include(s) a vibrato modulator (e.g., vibrato modulator 220-*a*) which generates a vibrato or frequency-control parameter (e.g., frequency-control parameter 222-*a*). In some implementations, the vibrato modulator (e.g., vibrato modulator 220-*a*) obtains a base frequency or pitch (e.g., a base frequency such as 50 Hz, 100 Hz, or any suitable frequency in the range of 50 Hz to 4 kHz) and modulates the base frequency in accordance with the signal value (e.g., amplitude, intensity and/or power) of the time-domain signal (e.g., time-domain signal 218). In other implementations, the vibrato modulator generates a vibrato or frequency-control parameter in accordance with the signal value of the time-domain signal (e.g., time-domain signal 218) that does not incorporate the base frequency or pitch. The amount of vibrato, as represented by the vibrato or frequency-control parameter, controls variations in frequency in the synthesized audio signal (i.e., the representation of an acoustic signal corresponding to the time-domain signal).

In some embodiments, signal modulator(s) 140/142 include(s) a vowel modulator (e.g., vowel modulator 220-*b*) which generates a vowel-control parameter (e.g., vowel-control parameter 222-*b*). In some implementations, a vowel modulator (e.g., vowel modulator 220-*b*) selects a sequence of acoustic waveform patterns from a set of N (e.g., N is an integer in the range of 2 to 15, such as N=12) acoustic waveform patterns comprising a sequence of phoneme waveform patterns (e.g., phoneme patterns corresponding to sounds in spoken language). In some implementations, the phoneme patterns include a plurality of vowel waveform patterns, and optionally include phoneme patterns (e.g., "sss" or "vvv") that are not vowel waveform patterns. In some implementations, each of the phoneme patterns is distinguished from the other phoneme waveform patterns in the set with respect to acoustic characteristics such as formants. In some embodiments, vowel modulator (e.g., vowel modulator 220-*b*) modulates a rate at which the acoustic waveform (e.g., vowel waveform) patterns are sequentially selected in accordance with the signal value (e.g., amplitude, intensity and/or power) of the time-domain signal. For example, vowel modulator (e.g., vowel-control parameter 222-*b*) modulates a rate at which acoustic waveform patterns from a set of 12 acoustic waveform patterns are sequentially selected in accordance with the signal value (e.g., amplitude) of the time-domain signal (e.g., time-domain signal 218). For example, an increase in signal value (e.g., amplitude) of the time-domain signal (e.g., time-domain signal 218), causes vowel modulator (e.g., vowel-control parameter 222-*b*) to sequentially select acoustic waveform patterns from a set of 12 acoustic waveform patterns more rapidly or at an increased rate; and conversely, a decrease in signal value (e.g., amplitude) of the time-domain signal (e.g., time-domain signal 218), causes vowel modulator (e.g., vowel-control parameter 222-*b*) to sequentially select acoustic waveform patterns from a set of 12 acoustic waveform patterns more gradually (e.g., slowly) or at a decreased rate.

In some embodiments, signal modulator(s) 140/142 include(s) an intensity modulator (e.g., intensity modulator 220-*c*) which generates an intensity-control parameter (e.g., intensity-control parameter 222-*c*). For example, an intensity modulator (e.g., intensity modulator 220-*c*) computes a time-varying amplitude value in accordance with the signal value (e.g., amplitude, intensity and/or power) of the time-domain signal (e.g., time-domain signal 218) and generates a time-varying intensity-control parameter (e.g., intensity-control parameter 222-*c*) corresponding to the computed time-varying amplitude value. In some implementations, an increase in signal value (e.g., amplitude) of the time-domain signal (e.g., time-domain signal 218), causes the time-varying amplitude value—and corresponding time-varying intensity-control parameter (e.g., intensity-control parameter 222-*c*)—computed by intensity modulator (e.g., intensity modulator 220-*c*) to increase. Conversely, a decrease in signal value of the time-domain signal (e.g., time-domain signal 218), causes the time-varying amplitude value—and corresponding time-varying intensity-control parameter (e.g., intensity-control parameter 222-*c*)—computed by intensity modulator (e.g., intensity modulator 220-*c*) to decrease.

In some embodiments, signal modulator(s) 140/142 include(s) a pitch modulator (e.g., pitch modulator 220-*d*) which generates a pitch-control parameter (e.g., pitch-control parameter 222-*d*). In some embodiments, pitch modulator (e.g., pitch modulator 220-*d*) selects a base frequency (e.g., corresponding to an acoustic pitch) in accordance with a spatial location of sensing the time-domain signal. In some embodiments, pitch modulator (e.g., pitch modulator 220-*d*) generates a time-varying pitch-control parameter in accordance with the selected base frequency and the signal value (e.g., amplitude, intensity and/or power) of the time-domain signal (e.g., time-domain signal 218, FIG. 2B). For example, pitch modulator (e.g., pitch modulator 220-*d*) selects a base frequency (e.g., a pitch) in accordance with a spatial location in the brain of sensing (e.g., by way of sensor(s) 110/112 located at different spatial locations in the brain) of the time-domain signal (e.g., sensor time-domain signal 201, FIG. 2A). For example, for a time-domain signal obtained from the left hemisphere in the brain, pitch modulator (e.g., pitch modulator 220-*d*) selects a lower base frequency (e.g., a frequency corresponding to the pitch of baritone voice); for a time-domain signal obtained from the right hemisphere in the brain, pitch modulator (e.g., pitch modulator 220-*d*) selects a higher base frequency (e.g., a frequency corresponding to the pitch of a tenor voice); and for a time-domain signal obtained from the heart, pitch modulator (e.g., pitch modulator 220-*d*) selects a still higher base frequency (e.g., a frequency corresponding to the pitch of soprano voice). More generally, in some implementations, when more than one time-domain signal is obtained from distinct sensors on a human body (e.g., distinct intracranial sensors in the brain, distinct extra-cranial sensors, and/or distinct ECG sensors), each time-domain signal is assigned a distinct base frequency so as to enable a listener to distinguish between the "voices" (acoustic signals or acoustic signal portions) corresponding to the distinct sensors and their time-domain signals.

In some embodiments, signal modulator(s) 140/142 generates, obtains or otherwise provides one or more sonic identity parameters 222-*e*. In some embodiments, signal modulator(s) 140/142 select(s) a sonic identity (for example, specific defining acoustic characteristics; e.g., acoustic characteristics associated with specific musical instruments) in accordance with a respective time-domain signal (e.g., a time-domain signal corresponding to a spatial location in the brain of sensing or a spatial location in the heart of sensing by way of sensors 110/112 located at different spatial locations in the brain and heart, respectively) and generates, obtains or otherwise provides one or more sonic identity parameter 222-*e* in accordance with the selected sonic identity. For example, for a time-domain signal obtained from the left hemisphere in the brain, a signal modulator(s) 140 selects a sonic identity corresponding to the sonic identity of (e.g., acoustic characteristics defining or associated with) a violin; for a time-domain signal obtained from the right hemisphere in the brain, a signal modulator(s) 140 selects a sonic identity corresponding to the sonic identity of (e.g., acoustic characteristics defining or associated with) a guitar; and for a time-domain signal obtained from the heart, a signal modulator(s) 142 selects a sonic identity corresponding to the sonic identity of (e.g., acoustic characteristics defining or associated with) a clarinet. More generally, in some implementations, when more than one time-domain signal is obtained from distinct sensors on a human body (e.g., from distinct intracranial sensors in the brain, or from distinct extra-cranial sensors, or from distinct ECG sensors), each time-domain signal is assigned a distinct sonic identity (e.g., and a corresponding set of one or more sonic identity parameters 222-e), so as to enable a listener to distinguish between the "voices" (acoustic signals or acoustic signal portions) corresponding to the distinct sensors and their time-domain signals.

One or more of the plurality of time-varying acoustic parameters (e.g., frequency-control parameter 222-a, vowel-control parameter 222-b, and/or intensity-control parameter 222-c) is modulated in accordance with at least the signal value (e.g., amplitude, intensity, and/or power) of the time-domain signal (e.g., time-domain signal 218, FIG. 2B, produced by signal conditioning module 130/132).

A synthesizer module (e.g., synthesizer module 150/152) combines the concurrently generated set of acoustic parameters (e.g., the acoustic parameters produced by signal modulator(s) 140/142 described above) to produce a representation of an acoustic signal (e.g., representation of acoustic signal 230) corresponding to the time-domain signal (e.g., time-domain signal 218, FIG. 2B, produced by signal conditioning module 130/132). In some embodiments, synthesizer module 150/152 is a music synthesizer or a music synthesizer module, for example a frequency modulation synthesizer (e.g., frequency modulation synthesizer 224). In some embodiments, a frequency modulation synthesizer (e.g., frequency modulation synthesizer 224) uses frequency modulation synthesis, controlled by the concurrently generated set of acoustic parameters, to generate a representation of an acoustic signal 230. For example, the frequency modulation synthesizer (e.g., frequency modulation synthesizer 224) modifies the timbre (e.g., the quality) of a waveform by frequency modulating it with a modulating signal. With respect to frequency modulation synthesis, U.S. Pat. No. 4,018,121, "Method of synthesizing a musical sound" is hereby incorporated by reference in its entirety.

As shown in FIG. 2D, in some embodiments, a plurality of representations of acoustic signals 230 (e.g., representation of acoustic signal 230-a, 230-b, 230-c, 230-d, and 230-e) are passed to a combiner module 170 and are combined using a summing unit 175 (e.g., a summing amplifier or a software implementation thereof) to produce a combined acoustic signal 240. In some embodiments, combiner module 170 includes one or more sub-modules configured to perform post-processing of the plurality of representations of acoustic signals 230 (e.g., respectively weighting of each of the plurality of representations of acoustic signals) or of the combined acoustic signal 240 (e.g., compression, equalization, etc.).

As shown in FIG. 1, in some embodiments, signal modulator 140/142 and/or synthesizer module 150/152 are implemented in digital processor 160. In some implementations, signal modulator 140/142 and/or synthesizer module 150/ 152 are implemented in a digital signal processor, sometimes called a DSP. In some implementations, signal modulator 140/142 and/or synthesizer module 150/152 are implemented in circuitry. And, in some implementations, signal modulator 140/142 and/or synthesizer module 150/ 152 are implemented in software executed by a general purpose processor.

Figure 3A:
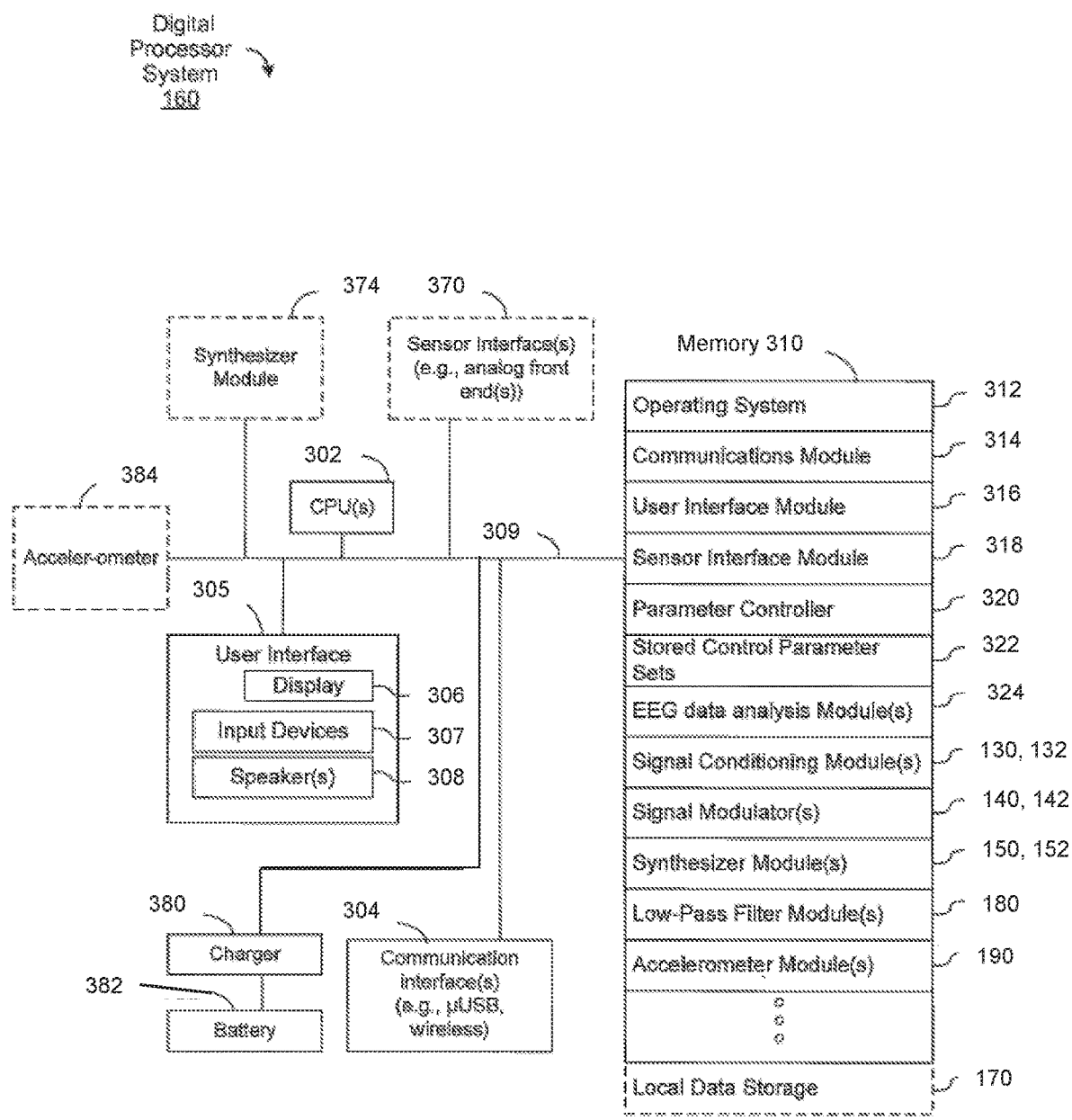
FIG. 3A is a block diagram illustrating a digital processor used for processing signals representing bodily functions, in accordance with some embodiments of the invention.
Figure 3B:
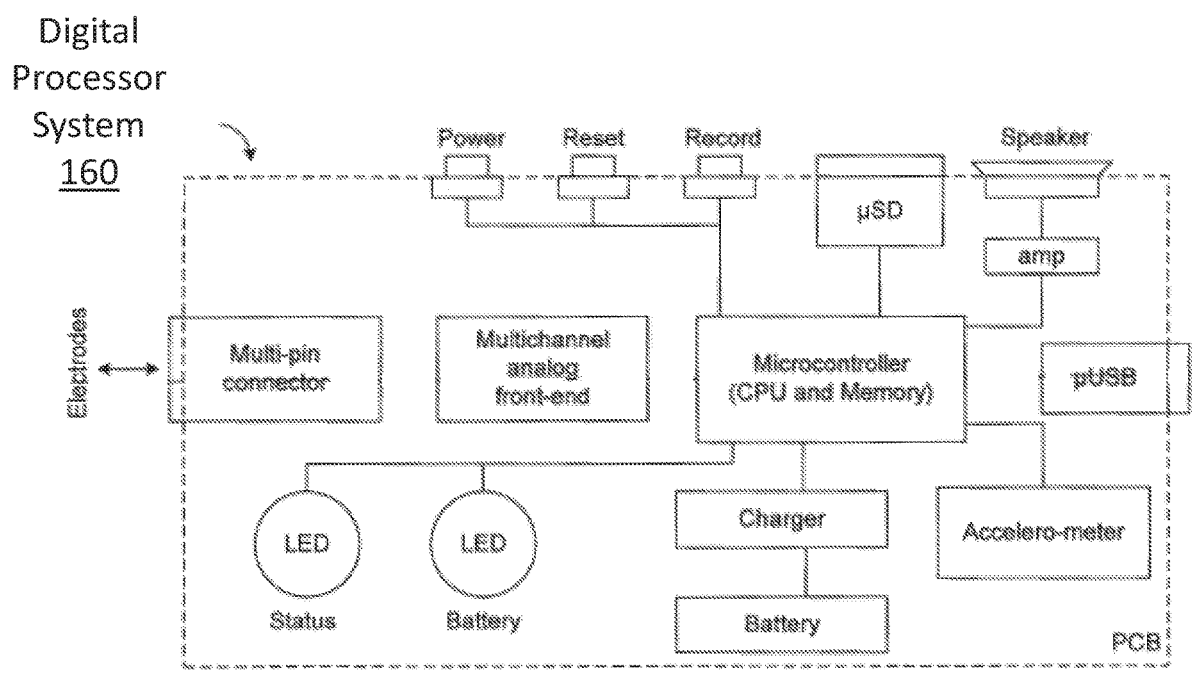
FIG. 3B is a schematic diagram of circuitry in a portable, pocket-sized handheld device for sonifying electrical signals, in accordance with some embodiments of the invention.

FIG. 3A is a block diagram illustrating digital processor system 160 in accordance with some embodiments, and FIG. 3B depicts an example of a set of components on a printed circuit board (PCB) that implement digital processor system 160. Digital processor system 160 typically includes one or more processing units (CPUs) 302 for executing modules, programs and/or instructions stored in memory 310 and thereby performing processing operations; one or more network or other communications interfaces 304 (e.g., a wired communication interface such as a USB port, micro-USB port, or the like, and/or a wireless communication interface); memory 310; and one or more communication uses 309 for interconnecting these components. The communication buses 309 optionally include circuitry (sometimes called a chipset) that interconnects and control communications between system components. Digital processor system 160 optionally includes a user interface 305 comprising a display 306, one or more input devices 307 (e.g., one or more buttons, and, optionally, one or more of a microphone, keypad, and touch screen, etc.), and one or more speakers 308 (e.g., for audio playback of acoustic signals corresponding to brain and/or heart activity). Display 306 optionally includes one or more LEDs, for example, one or more LEDs for indicating a status of digital processor system 160 (e.g., a steady blinking LED to indicate that EEG signals are being received and/or to indicate that accelerometer signals corresponding to mechanical movement of the subject are sufficiently low-amplitude to allow DSP 160 to produce valid sonification of EEG signals) and, in another example, an LED to indicate battery status (e.g., a red LED that is turned on when battery power is low, and/or a green LED that is turned on when an internal battery is charged and that blinks on and off in a predefined pattern when battery power is low).

As shown in FIG. 3B, in some embodiments, input devices 307 may include a power on/off button for powering digital processor system 160 on and off, a reset button for resetting digital processor system 160 to a predefined initial state, and a record button for starting and stopping recording of EEG data corresponding to a subject's brain activity. Furthermore, in some embodiments, input devices 307 include a microphone for receiving and recording a user's spoken comments made just prior to, or while, DSP 160 recording EEG data corresponding to a subject's pressing the "record" button shown in FIG. 3B, digital processor system 160 records any spoken comments by the user for a predefined period (e.g., 5 to 10 seconds following the button press), and also records EEG data corresponding to the subject's brain activity until the user presses the record button a second time, or until a predefined period of time elapses (e.g., 5 minutes), or until a predefined period of time (e.g., 5 minutes) elapses during which the device (digital processor system 260) does not receive electrical signals corresponding to abnormal brain activity.

Digital processor system 160 optionally includes sensor interfaces 307 for interfacing with sensors 110 (FIG. 1) and/or analog front end 120 (FIG. 1) and synthesizer module 374 for combining concurrently generated acoustic parameters to produce a representation of an acoustic signal corresponding to one or more time-domain signals. As explained in more detail below, in some embodiments, sensors 110 are located, at least in part, within the same housing that holds digital processor system 160, while in some other embodiments, sensors 110 are located external to that housing and are coupled to digital processor system 160 via one or more electrical connectors and sensor interface(s) 370.

In some embodiments, sensor interface 370 includes an impedance detector that detects whether sensors 110 (e.g., electrodes) are attached to the subject. In some embodiments, when DSP 160 determines that the impedance looking into sensors 110 is below an impedance threshold, DSP 160 determines that sensors 110 are attached to the subject. On the other hand, when DSP 160 determines that the impedance looking into the sensors 110 is above the impedance threshold, DSP determines that sensors 110 are not attached to the subject (e.g., the circuit formed by DSP 160 and sensors 110 is an open circuit).

Digital processor system 160 optionally includes a movement sensor 384 (e.g., a 3-axis accelerometer or an inertial measurement unit (IMU)) that measures mechanical movement of the subject and/or the device (e.g., produce one or more electrical signals corresponding to mechanical movement of the subject and/or device).

Digital processor system 160 optionally (and typically) includes a battery 382 (e.g., a rechargeable battery) and charger 380, to provide power to digital processor system 160 and enable operation of digital processor system 160 without connection to an external power source (except to charge battery 382). In some embodiments, battery 382 is charged via charger 380, when an external power source is connected to system 160 via a USB port or micro-USB port of the device.

Memory 310 may include high-speed random access memory, such as DRAM, SRAM, DDR RAM or other random access solid state memory devices; and optionally includes non-volatile memory, such as one or more magnetic disk storage devices, optical disk storage devices, flash memory devices, or other non-volatile solid state storage devices. Memory 310 optionally includes one or more storage devices remotely located from the CPUs 302, memory 310, or alternately the non-volatile memory devices within memory 310, comprises a non-transitory computer readable storage medium. In some embodiments, memory 310, or the computer readable storage medium of memory 310 stores the following programs, modules and data structures, or a subset thereof:

Operating system 312 that may include procedures for handling various basic system services and for performing hardware dependent tasks;

Network communication module 314 that may be used for connecting digital processor system 160 to other computers via the one or more communication network interfaces 309 (wired or wireless) and one or more communication networks, such as the Internet, other wide area networks, local area networks, metropolitan area networks, and so on;

User interface module 316 that may receive commands from the user via one or more input devices 307 of user interface 315, generates user interface objects in display device 306, and optionally generates representations of signals corresponding to brain and/or heart activity, information corresponding to sensors and sensor interfaces, and information related to the configuration of body interface system 300 for display on display device 306;

Parameter controller 320 that may control (e.g., executes instructions for) the generation of the set of acoustic parameters, including a plurality of time-varying acoustic parameters (such as a frequency-control parameter (sometimes called a vibrato parameter), a vowel-control parameter, an intensity-control parameter, a pitch-control parameter, and/or an identity-control parameter). Parameter controller 320 may also interact with sensor interfaces 370 to facilitate selection of parameters (e.g., any of the aforementioned parameters) and corresponding parameter values based on the sensors selected and sensor signals obtained (e.g., based on a spatial location in the brain and/or heart from which the time-domain signal is sensed). For example, sensor interface module 318 may interface with parameter controller 320 to communicate a set of parameters, corresponding to one or more of pitch, vowel selection, vibrato, intensity (amplitude), and sonic identity parameter, selected in accordance with the selected sensor, or in accordance with a spatial location in the brain and/or heart of sensing a time-domain signal;

Stored control parameter sets 322 that may include one or more sets of signal parameters or values corresponding to signal parameters (for example, one or more values of base frequencies, a set of acoustic waveform patterns corresponding to phoneme patterns, one or more sonic identities, etc.);

Signal conditioning modules 130, 132 may up-sample and low pass filter the sensor time-domain signal to produce a time-domain signal representing brain and/or heart activity;

Signal modulators 140, 142 may concurrently generate a set of acoustic parameters, including a plurality of time-varying acoustic parameters, for example, a frequency-control parameter, a vowel-control parameter, a time-varying intensity-control parameter, a pitch-control parameter, and/or a sonic identity parameter;

Synthesizer modules 150, 152 may combine the concurrently generated set of acoustic parameters to produce a representation of an acoustic signal corresponding to the time-domain signal;

Low-pass filter modules 180 may configure and/or apply a low-pass filter to electrical signals received from sensor interface 370 to remove electrical noise that results from convulsive muscle movements (e.g., low-pass filter module applies a fixed-configuration low-pass filter, or a low-pass filter configured by system 160 (as discussed in more detail below), or a user-selectable low-pass filter, which is in addition to the low-pass filter applied by signal conditioning module 130, 132);

Movement sensor modules 190 may process movement information from movement sensor 384 and optionally configure and/or apply filters to remove mechanical movement artifacts in electrical signals received from sensor interface 370; and Optional local data storage 170 that may store data corresponding to the one or more electrical signals (e.g., data storage 170 stores raw EEG data and/or audio data so that the data can be reviewed later by, e.g., a specialist). In some implementations, data storage 170 includes a removable non-volatile memory card, such as a micro SD flash memory card (see "μSD" in FIG. 3B, which represents a micro-SD card "reader" for receiving and interfacing a micro SD flash memory card to a microcontroller). As an alternative, or in addition to data storage 170, digital processor system 160 may communicate with cloud-based storage (e.g., storage that is remote from the device) to store data corresponding to the one or more electrical signals.

Each of the above identified elements is optionally stored in one or more of the previously mentioned memory devices of digital processor system 160, and corresponds to a set of instructions for programming a function described above. The above identified modules or programs (i.e., sets of instructions) need not be implemented as separate software programs, procedures or modules, and thus various subsets of these modules is optionally combined or otherwise rearranged in various embodiments. In some embodiments, memory 310 optionally stores a subset of the modules and data structures identified above. Furthermore, memory 310 optionally stores additional modules and data structures not described above. For example, in some embodiments, memory 310 may store one or more EEG data analysis modules 324, for analyzing EEG data received by digital processor system 160 and conveying one or more results to a user of the device (e.g., via display 306 or speaker(s) 308), or to a remote device or user via communications interface 304. The one or more EEG data analysis modules 324, if provided, may use any of a number of seizure detection methods, including EEG data analysis methods previously developed or developed in the future.

Although FIGS. 3A-3B show digital processor system 160, FIGS. 3A-3B are intended to provide functional descriptions of the various features which are optionally present in a digital processor system, and not as a structural schematic of the embodiments described herein. In practice, and as recognized by those of ordinary skill in the art, items shown separately could be combined and some items could be separated. For example, some items shown separately in FIGS. 3A-3B could be implemented on a single digital processor system and single items could be implemented by one or more digital processor systems. The actual number of digital processor systems used to implement digital processor system 160 and how features are allocated among then may vary from one implementation to another.

Figure 4A:
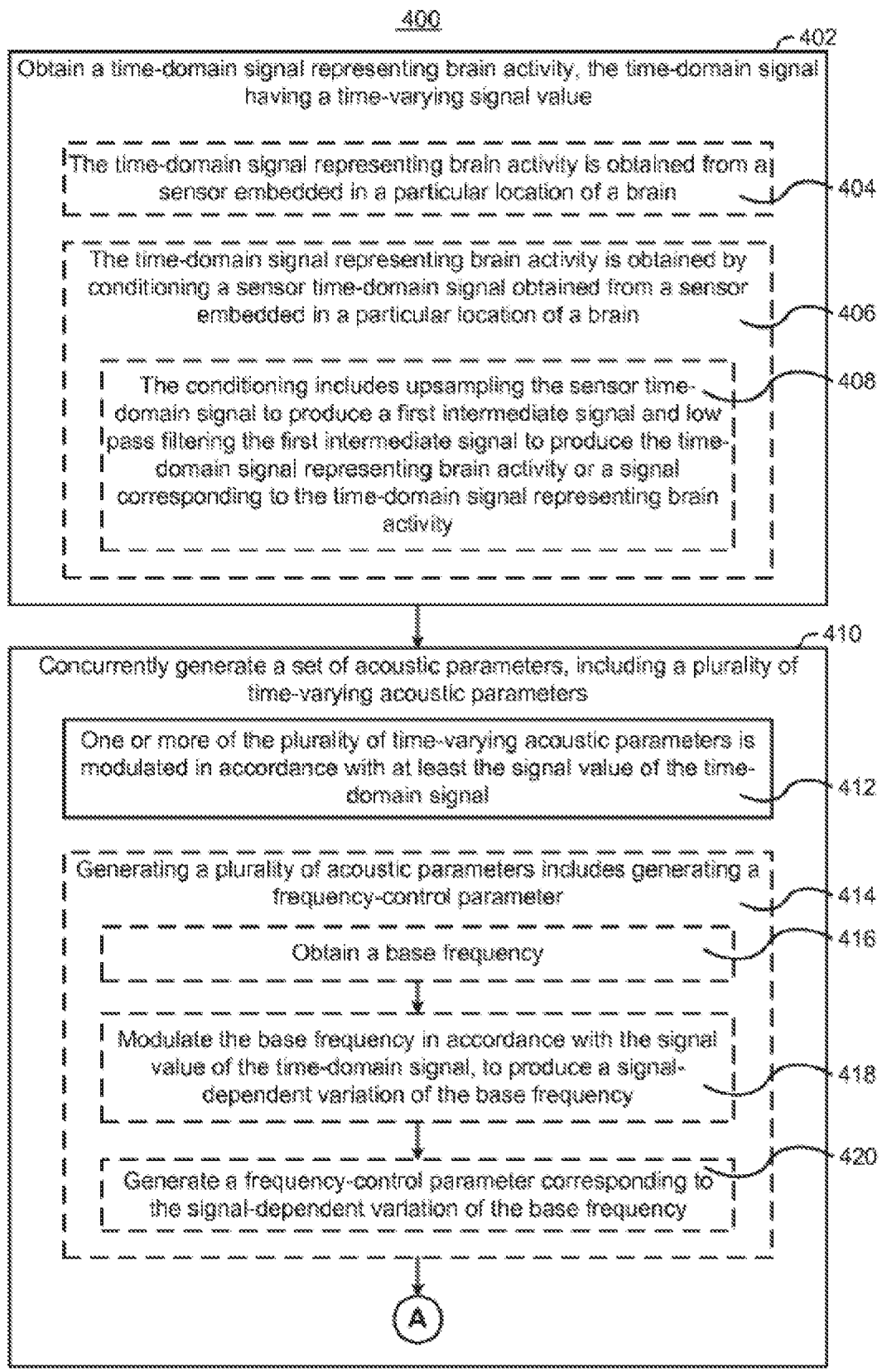
FIGS. 4A-4C include a flow chart illustrating a method for sonifying brain electrical activity, in accordance with some embodiments.
Figure 4B:
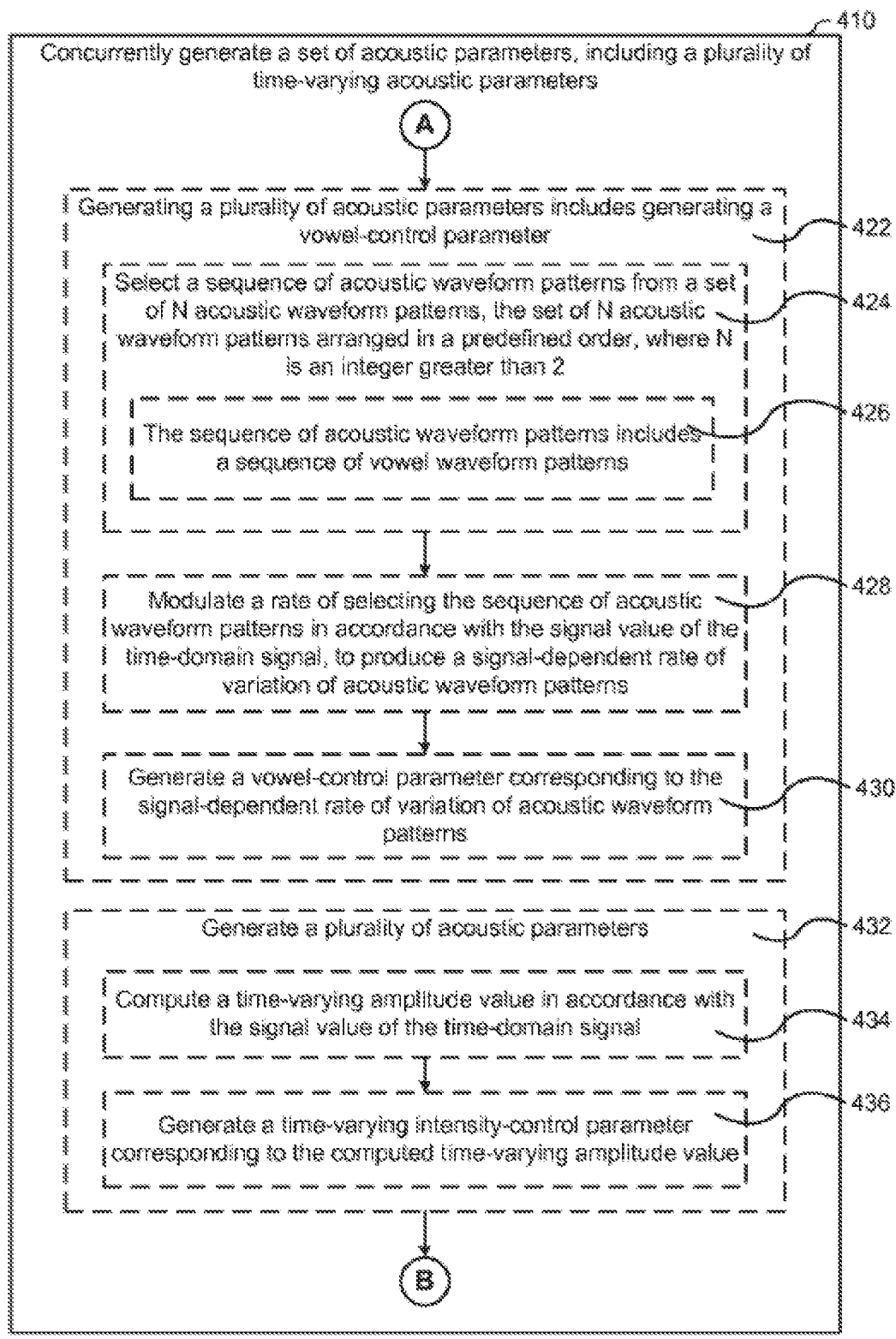
Figure 4C:
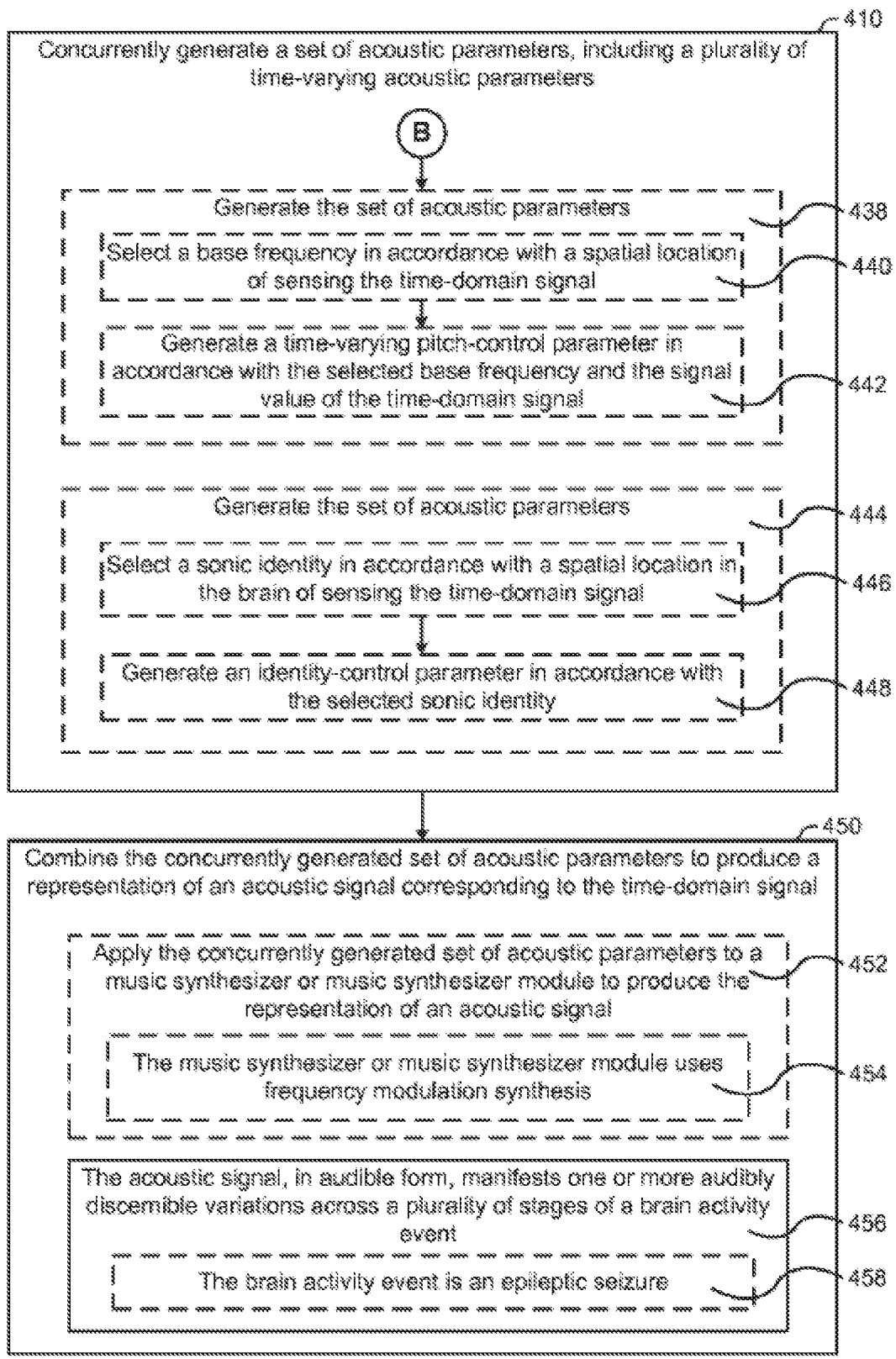

FIG. 4 is a flowchart representing method 400 for sonifying brain electrical activity, according to certain embodiments of the invention. Method 400 is optionally governed by instructions that are stored in a computer readable storage medium and that are executed by a digital processor system (or, optionally, one or more digital processor systems) (e.g., digital processor system 160). Each of the operations shown in FIG. 4 optionally corresponds to instructions stored in a computer memory or computer readable storage medium. The computer readable storage medium optionally includes a magnetic or optical disk storage device, solid state storage devices such as flash memory, or other non-volatile memory device or devices. The computer readable instructions stored on the computer readable storage medium are in source code, assembly language code, object code, or other instruction format that is interpreted by one or more processors.

The digital processor system obtains (402) a time-domain signal (e.g., time-domain signal 218, FIG. 2B) representing brain activity, the time-domain signal having a time-varying signal value. In some embodiments, the time-domain signal representing brain activity is obtained (404) from a sensor embedded in a particular location of a brain. For example, as explained with reference to FIG. 1 and FIG. 2B, time-domain signal 218 (FIG. 2B) is obtained from sensor(s) 110 embedded in a particular location of a brain (e.g., Intracranial Sensor 110-2). In some implementations, intracranial sensor 110-2 is formed (e.g., fabricated) on a needle embedded in the brain with one or more sensing elements located along the length and/or circumference of the needle and differential voltages (e.g., differences in voltage values) are measured between two measurement locations (e.g., between two sensing elements) to produce a differential voltage signal corresponding optionally to sensor time-domain signal 201, FIG. 2a or to time-domain signal 218, FIG. 2B.

In some embodiments, the time-domain signal representing brain activity is obtained (406) by conditioning a sensor time-domain signal obtained from a sensor embedded in a particular location of a brain. For example, as shown in FIG. 1 and FIGS. 2A-2B, sensor time-domain signal 201 is obtained from a sensor embedded in a particular location of a brain (e.g., from intracranial sensor 110-2, FIG. 1) and—after optionally being pre-processed by analog front end 120 to produce filtered sensor time-domain signal 207—is conditioned by signal conditioning module 130.

In some embodiments, the conditioning includes (408) upsampling the sensor time-domain signal to produce a first intermediate signal and low pass filtering the first intermediate signal to produce the time-domain signal representing brain activity or a signal corresponding to the time-domain signal representing brain activity. For example, as shown in FIG. 2B, filtered sensor time-domain signal 207—after conversion from an analog signal to a corresponding digital signal—is upsampled (e.g., by upsampler 212, FIG. 2B) to produce a first intermediate signal (e.g., first intermediate signal 214, FIG. 2B). For example, as explained above, if the original sampling rate of the digital representation of the analog filtered sensor time-domain signal corresponds to 500 Hz, the first intermediate signal (e.g., first intermediate signal 214) produced by upsampler 212 has a sampling rate used in conventional audio applications (e.g., 48 kHz). First intermediate signal 214 is then low pass filtered (e.g., by digital low pass filter(s) 216, FIG. 2B) to produce the time-domain signal representing brain activity or a signal corresponding to the time-domain signal representing brain activity (e.g., time-domain signal 218, FIG. 2B).

The digital processor system concurrently generates (410) a set of acoustic parameters (e.g., see operations 412-448), including a plurality of time-varying acoustic parameters. In this context, parameters are "concurrently generated" even if they are literally generated serially by single-threaded processor, when the resulting parameters are used or applied concurrently for generating an audio signal, or a representation of an audio signal. Typically, two or more concurrently generated parameters are generated or updated in response to a stream of digital signal values corresponding to the time-domain signal.

One or more of the plurality of time-varying acoustic parameters is modulated (412) in accordance with at least the signal value of the time-domain signal. For example, as explained above with reference to FIG. 2C, signal modulator(s) 140 (optionally included in digital processor system 160) concurrently generate(s) a set of acoustic parameters, including a plurality of time-varying acoustic parameters. In some embodiments, as described in relation to FIG. 2C above, the plurality of acoustic parameters includes a vibrato or frequency-control parameter (e.g., frequency-control parameter 222-a), a vowel-control parameter (e.g., vowel-control parameter 222-b), and/or a time-varying amplitude or intensity-control parameter (e.g., intensity-control parameter 222-c). In some embodiments, the set of acoustic parameters includes a pitch-control parameter (e.g., pitch-control parameter 222-d) and/or a sonic identity parameter (e.g., sonic identity parameter 222-e).

In some embodiments, generating a plurality of acoustic parameters includes (414) generating a vibrato or frequency-control parameter (as described herein with respect to operations 416-420). For example, as described above with reference to FIG. 2C, signal modulator(s) 140 (optionally included in a digital processor system) includes vibrato modulator 220-a, which generates frequency-control parameter 222-a.

In some embodiments, the digital processor system obtains (416) a base frequency. In some embodiments, the digital processor system modulates (418) the base frequency in accordance with the signal value of the time-domain signal, to produce a signal-dependent variation of the base frequency. In some embodiments, the digital processor system generates (420) a frequency-control parameter corresponding to the signal-dependent variation of the base frequency. For example, as explained above, vibrato modulator (e.g., Vibrato Modulator 220-a, FIG. 2C) generates a control parameter for controlling the amount of vibrato (which can be considered to be the amount of frequency variation) produced by a music or audio synthesizer. In some implementations (e.g., implementations in which pitch and vibrato are controlled during audio synthesis by separate parameters) the frequency-control parameter is independent of the base frequency or pitch, while in other implementations the frequency-control parameter incorporates the base frequency or pitch.

In some embodiments, generating a plurality of acoustic parameters includes (422) generating a vowel-control parameter (as described herein with respect to operations 424-430). For example, as shown in FIG. 2C, signal modulator(s) 140 (optionally included in digital processor 160) comprise(s) vowel modulator 220-b which generates vowel-control parameter 222-b.

In some embodiments, a digital processor (e.g., digital processor 160) sequentially selects (424) acoustic waveform patterns from an ordered set of N acoustic waveform patterns, the set of N acoustic waveform patterns arranged in a predefined order, where N is an integer greater than 2. In some embodiments, the sequence of selected acoustic waveform patterns includes (426) a sequence of vowel waveform patterns. In some embodiments, a digital processor (e.g., digital processor 160) modulates (428) a rate of sequentially selecting acoustic waveform patterns in accordance with the signal value of the time-domain signal, to produce a signal-dependent rate of variation of acoustic waveform patterns. In some embodiments, a digital processor (e.g., digital processor 160) generates (430) a vowel-control parameter corresponding to the signal-dependent rate of variation of acoustic waveform patterns.

For example, as described above, vowel modulator (e.g., vowel-control parameter 222-b) modulates a rate of sequentially selecting acoustic waveform patterns from a set of 12 acoustic waveform patterns in accordance with the signal value of the time-domain signal (e.g., time-domain signal 218, FIG. 2C). For example, for an increase in signal value of the time-domain signal (e.g., time-domain signal 218), vowel modulator (e.g., vowel-control parameter 222-b) selects (e.g., scans through) a sequence of acoustic waveform patterns from a set of 12 acoustic waveform patterns more rapidly or at an increased rate; conversely, for a decrease in signal value of the time-domain signal (e.g., time-domain signal 218), vowel modulator (e.g., vowel-control parameter 222-b) selects (e.g., scans through) a sequence of acoustic waveform patterns from a set of 12 acoustic waveform patterns more gradually (e.g., slowly) or at a decreased rate.

In some embodiments, the digital processor system generates (432) a plurality of acoustic parameters, as described herein with respect to operations 434-436. In some embodiments, the digital processor system computes (434) a time-varying amplitude value in accordance with the signal value of the time-domain signal. In some embodiments, the digital processor system generates (436) a time-varying intensity-control parameter corresponding to the computed time-varying amplitude value.

For example, as described above in relation to FIG. 2C, an intensity modulator (e.g., intensity modulator 220-c, FIG. 2C) computes a time-varying amplitude value in accordance with the signal value of the time-domain signal (e.g., time-domain signal 218, FIG. 2c) and generates a time-varying intensity-control parameter (e.g., intensity-control parameter 222-c, FIG. 2C) corresponding to the computed time-varying amplitude value. In some implementations, for an increase in signal value of the time-domain signal (e.g., time-domain signal 218), the time-varying amplitude value—and corresponding time-varying intensity-control parameter (e.g., intensity-control parameter 222-c)—computed by intensity modulator (e.g., intensity modulator 220-c) increases. Conversely, for a decrease in signal value of the time-domain signal (e.g., time-domain signal 218), the time-varying amplitude value—and corresponding time-varying intensity-control parameter (e.g., intensity-control parameter 222-c)—computed by intensity modulator (e.g., intensity modulator 220-c) decreases.

In some embodiments, the digital processor system generates (438) the set of acoustic parameters, as described herein with respect to operations 440-442. In some embodiments, the digital processor system selects (440) a base frequency in accordance with a spatial location of sensing the time-domain signal. In some embodiments, the digital processor system generates (442) a time-varying pitch-control parameter in accordance with the signal value of the time-domain signal, and optionally in accordance with the selected base frequency. For example, as shown in FIG. 2C, signal modulator(s) 140 (optionally included in digital processor 160) comprise(s) pitch modulator 220-d which generates pitch-control parameter 222-d in accordance a signal value of the time-domain signal (e.g., time-domain signal 218), and optionally in accordance with a selected base frequency (e.g., corresponding to a spatial location of sensing the time-domain signal).

Without limitation with respect to other implementations, in some implementations the set of acoustic parameters are generated, in accordance with a set of instructions executed by one or more processors of a digital processor system, as described above. The following is an example of a pseudocode representation of instructions for generating the set of acoustic parameters, once per time period (e.g., once every 10 milliseconds), where SigVal is the signal value for the current time period:

```
// amplitude
amplitude.param=max(0.0, c1+c2*SigVal);
//pitch
pitch.param=ConvertMidiToFreq(c3-c4*SigVal);
//vibrato
vibrato-gain.param=pitch.param*(2^{c5}-1);
vibrato.param=vibrato.param+c6*SigVal;
vibrato.freq.param=max(0.0, min(c7, c8+vibrato.param));
//vowel vow=vow+(c9*SigVal);
vowel.param=integer (abs(vow)) modulo 12;
``` where, in one example, the following coefficient values are used: $c1=0.1$, $c2=20$, $c3=45$, $c4=5$, $c5=0.05$, $c6=4$, $c7=8.0$, c8=4.5, c9=20. Further, "ConvertMidiToFreq" is a function for converting a midi note to a frequency value, "max" is a function that outputs the maximum of its input values, "min" is a function that outputs the minimum of its input values, "abs" is a function that outputs the absolute value of its input, and "integer" is a function that outputs the integer portion of its input. In another example, in which two or more multiple time-domain signals are processed to produce a corresponding number of audio signals (sometimes called voices for ease of reference), one or more of the coefficients (e.g., c1 to c9 in the above example) are different for each of the different audio signals, thereby producing audio signals that are audibly distinct. In one example, coefficients c3 (corresponding to base frequency) and c6 (corresponding to amount of vibrato) and c9 (corresponding to rate at which the audio signal traverses a sequence of vowels or phonemes), have different values for each audio signal.

For example, as shown in FIG. 1, Sensor(s) 110 are located at different spatial locations in the brain for sensing the time-domain signal (e.g., Sensor Time-Domain Signal 201), and a base frequency (e.g., a pitch) is selected in accordance with a spatial location in the brain of sensing the time-domain signal. In this example, for a time-domain signal obtained from the left hemisphere in the brain, a lower base frequency (e.g., a frequency corresponding to the pitch of a baritone voice) is selected; whereas for a time-domain signal obtained from the right hemisphere in the brain, a higher base frequency (e.g., a frequency corresponding to the pitch of a tenor voice) is selected.

In some embodiments, the digital processor system generates (444) the set of acoustic parameters, as described with respect to operations 446-448. In some embodiments, the digital processor system selects (446) a sonic identity in accordance with a spatial location in the brain (or, alternatively, on the surface of the cranium) of sensing the time-domain signal. In some embodiments, the digital processor system generates (448) an identity-control parameter in accordance with the selected sonic identity. For example, as shown in FIG. 2C, Signal Modulator(s) 140 (optionally included in Digital Processor 160) comprise(s) Sonic Identity Modulator 220-e which generates Sonic Identity Parameter(s) 222-e in accordance with a selected sonic identity corresponding to a spatial location in the brain of sensing the time-domain signal.

For example, as shown in FIG. 1, Sensor(s) 110 are located at different spatial locations in the brain for sensing the time-domain signal (e.g., Sensor Time-Domain Signal 201), and a sonic identity is selected in accordance with a spatial location in the brain (or, alternatively, on the surface of the cranium) of sensing the time-domain signal. In this example, for a time-domain signal obtained from the left hemisphere in the brain, a sonic identity is selected corresponding to the sonic identity of (e.g., acoustic characteristics defining or associated with) a violin (or a first "voice"); whereas for a time-domain signal obtained from the right hemisphere in the brain, a sonic identity is selected corresponding to the sonic identity of (e.g., acoustic characteristics defining or associated with) a guitar (or a second "voice"). In some implementations, the sonic identity is simply the base frequency of each generated acoustic signal (or representation of an acoustic signal), while in some other implementations, the sonic identity determines both the base frequency and one or more parameters (e.g., multipliers, offsets, etc.) that are used while generating the acoustic parameters corresponding to each time-domain signal (e.g., corresponding to each sensor signal being sonified).

The digital processor system combines (450) the concurrently generated set of acoustic parameters to produce a representation of an acoustic signal corresponding to the time-domain signal. For example, as shown in FIG. 2C, synthesizer module 150 (optionally included in digital processor 160) combines the concurrently generated set of acoustic parameters generated by signal modulator(s) 140 to produce a representation of an acoustic signal (representation of acoustic signal 230) corresponding to the time-domain signal (e.g., time-domain signal 218).

In some embodiments, the digital processor system applies (452) the concurrently generated set of acoustic parameters to a music synthesizer or music synthesizer module to produce the representation of an acoustic signal. In some embodiments, the music synthesizer or music synthesizer module uses (454) frequency modulation synthesis. For example, as shown in FIG. 2C, synthesizer module 150 uses frequency modulation synthesis implemented on frequency modulation synthesizer 224.

The acoustic signal, in audible form, manifests (456) one or more audibly discernible variations across a plurality of stages of a brain activity event. In some embodiments, the brain activity event is (458) an epileptic seizure. For example, the acoustic signal corresponding to representation of acoustic signal 230, in audible form, manifests one or more audibly discernible variations (e.g., variations in vibrato, in rate of change of vowel, and/or in intensity) across a plurality of stages of a brain activity event. In some embodiments in which the brain activity event is an epileptic seizure, the acoustic signal in audible form manifests one or more audibly discernible variations (change in volume, pitch, rate of vowel change) across the stages (e.g., normal state, pre-ictal phase, seizure phase and post-ictal phase) of the epileptic seizure. For example, the acoustic signal is periodic and has higher amplitude during the seizure phase, and is chaotic (has lower or little periodicity) and has lower amplitude during the normal state.

In some implementations, the brain activity event for which brain electrical signals are sonified is not an epileptic seizure, and instead is a respective brain activity event that is the subject of analysis or monitoring. For example, in some implementations the brain activity event for which brain electrical signals are sonified comprises brain activity while the human subject performs various tasks (e.g., mental tasks, physical tasks, operating an apparatus, answering questions, playing a musical instrument, taking an exam, performing or attempting to perform multiple tasks or functions concurrently, etc.), brain activity associated with experiencing various external stimuli, brain activity associated with physiological functions, brain activity associated with various diseases, and the like.

Figure 5:
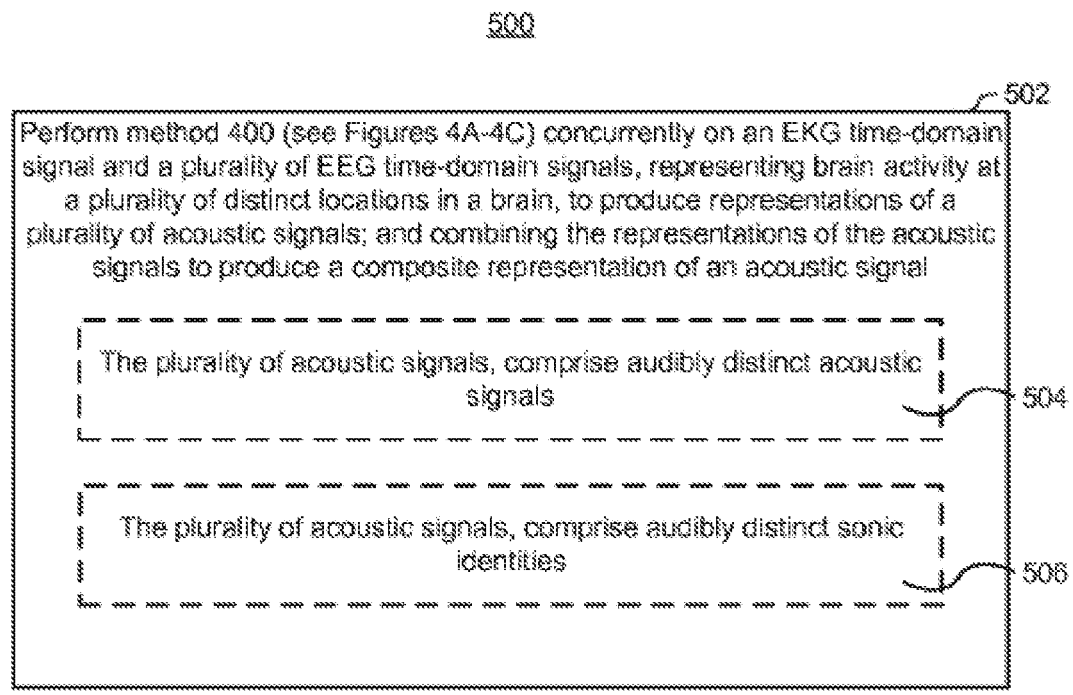
FIG. 5 includes a flow chart illustrating a method for sonifying brain electrical signals concurrently obtained from a plurality of distinct locations in the brain, in accordance with some embodiments.
Figure 6A:
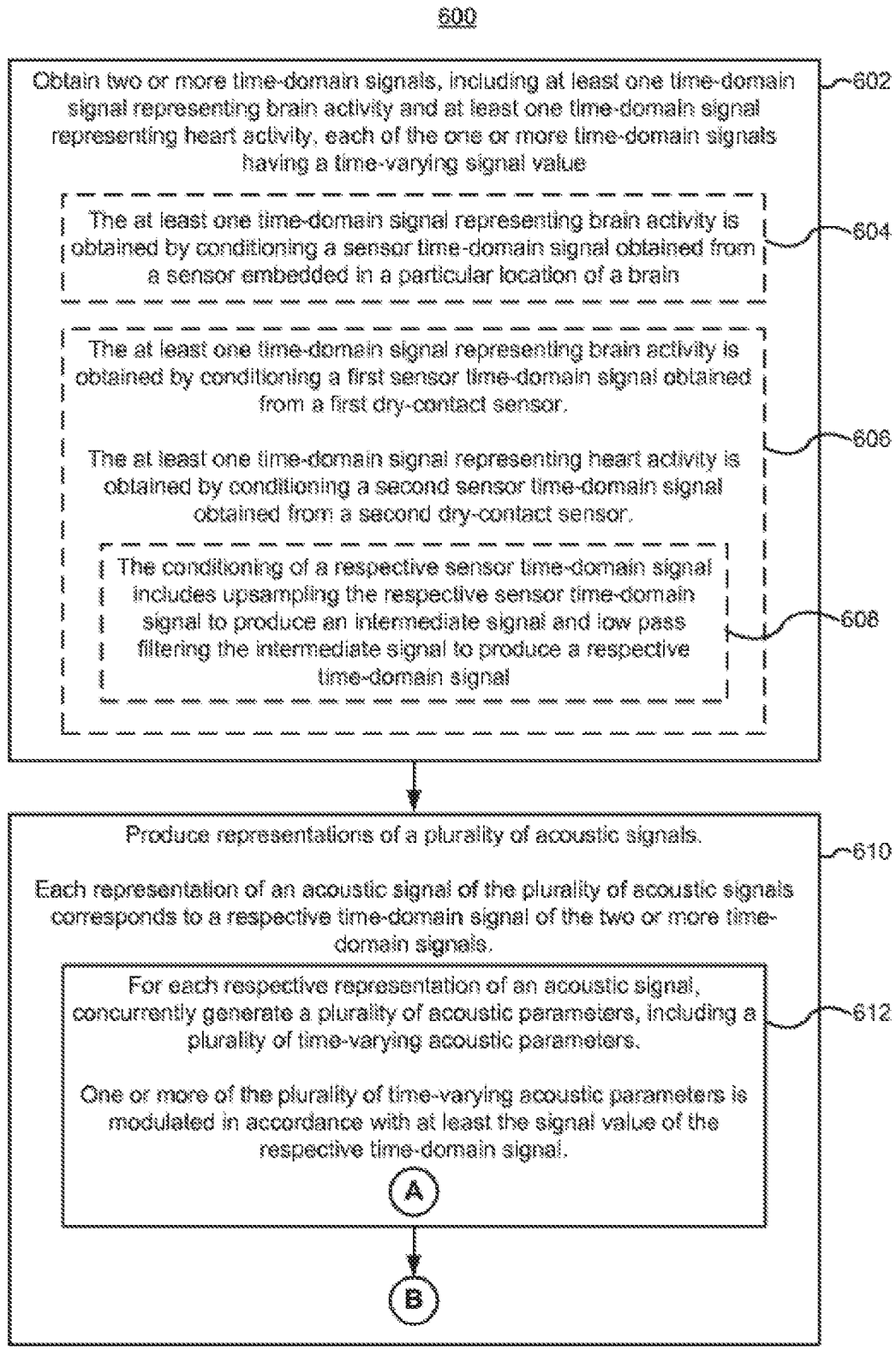
Figure 6B:
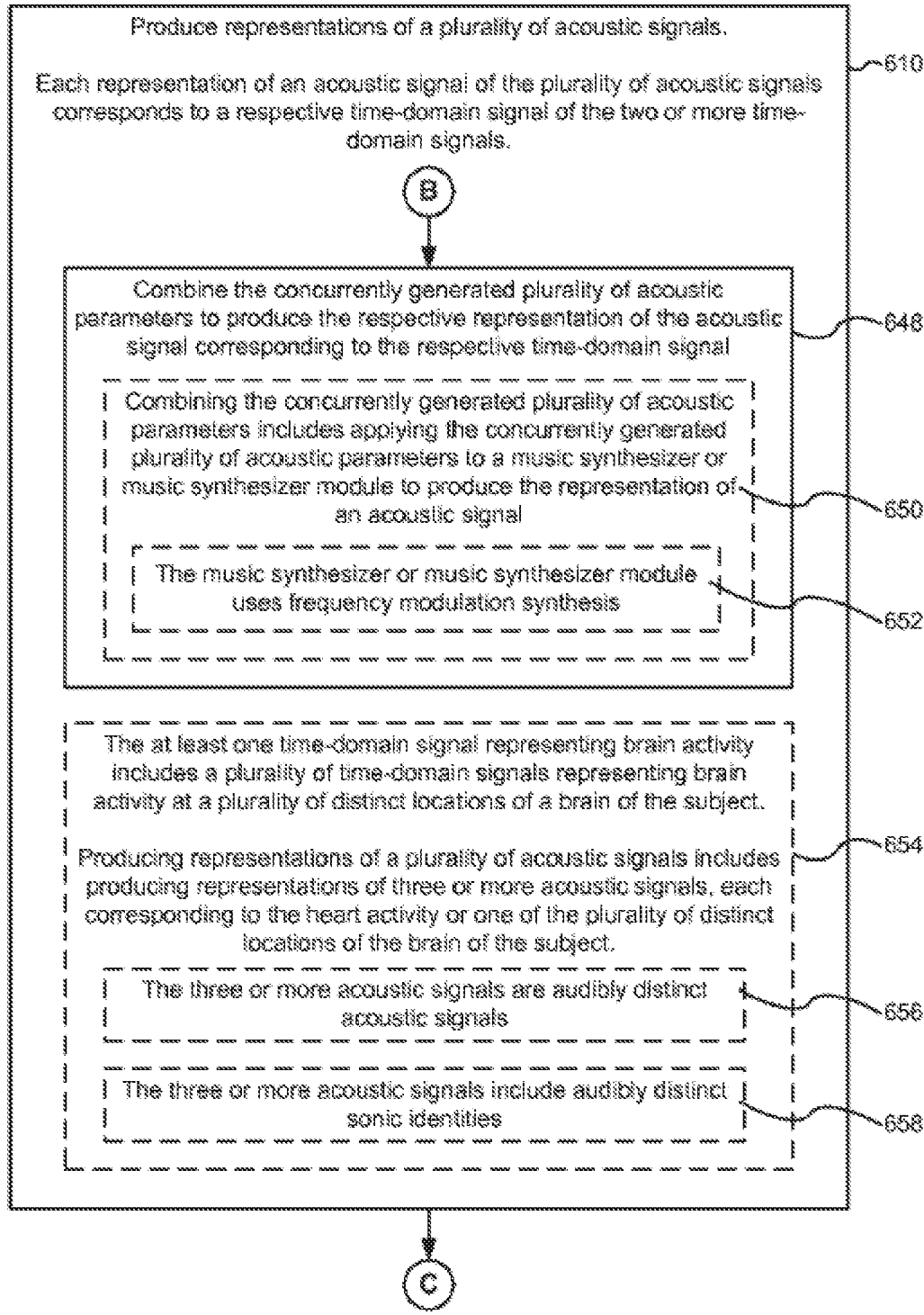
Figure 6C:
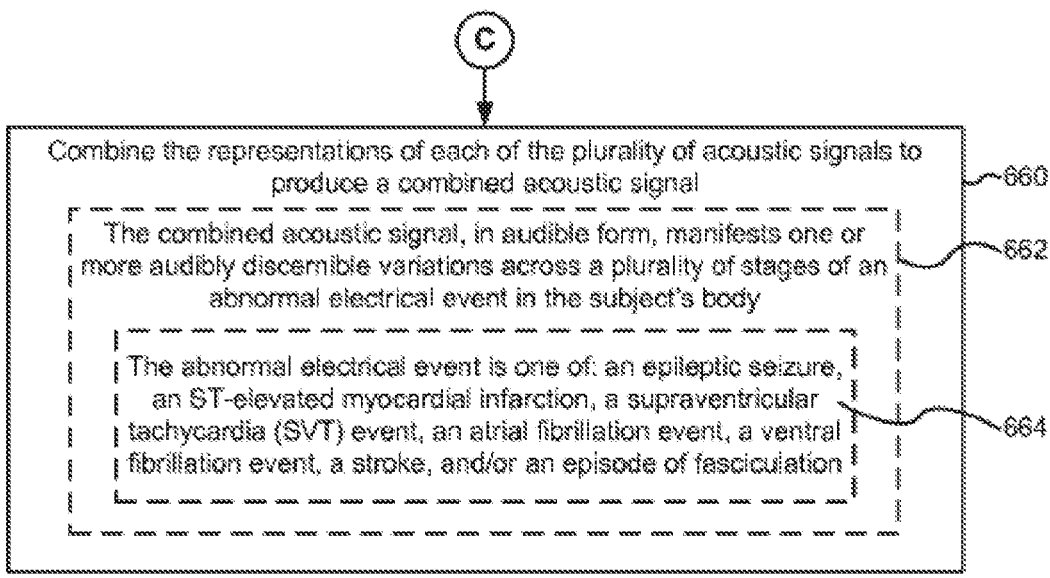
Figure 6D:
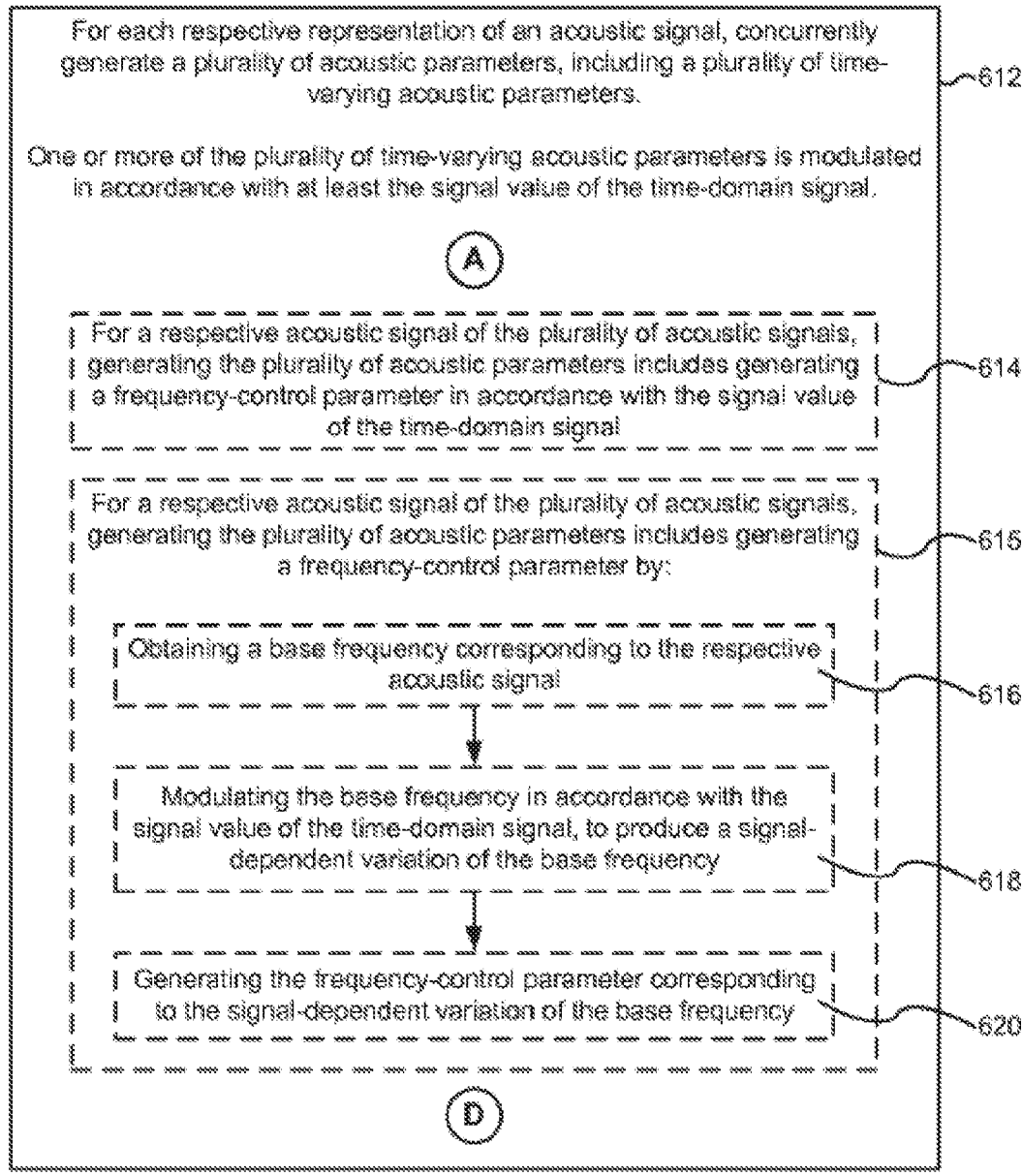

FIG. 5 is a flowchart representing method 500 for sonifying brain electrical signals concurrently obtained from a plurality of distinct locations in the brain, according to certain embodiments of the invention. Method 500 is optionally governed by instructions that are stored in a computer readable storage medium and that are executed by one or more processors of one or more digital processor systems. Each of the operations shown in FIG. 5 optionally corresponds to instructions stored in a computer memory or computer readable storage medium. The computer readable storage medium optionally includes a magnetic or optical disk storage device, solid state storage devices such as Flash memory, or other non-volatile memory device or devices. The computer readable instructions stored on the computer readable storage medium are in source code, assembly language code, object code, or other instruction format that is interpreted by one or more processors.

In some implementations, the digital processor system (e.g., digital processor 160, FIGS. 1, 3A, 3B) performs (502) method 400 (described herein with reference to FIGS. 4A-4C) concurrently on a plurality of time-domain signals representing brain activity at a plurality of distinct locations in a brain to produce representations of a plurality of acoustic signals, each corresponding to one of the plurality of distinct locations in the brain. For example, as shown in FIG. 1, digital processor 160 (FIGS. 1, 3A, 3B) performs the above-described method 400 concurrently on a plurality of time-domain signals (e.g., a plurality of sensor time-domain signal(s) 201, FIG. 2c, obtained from a plurality of sensor(s) 110, FIG. 1) representing brain activity at a plurality of distinct locations in a brain to produce representations of a plurality of acoustic signals (e.g., a plurality of representation of acoustic signal 230, FIG. 2C). In some embodiments, sensor(s) 110 (e.g., intracranial sensor 110-2), FIG. 1 include intracranial depth electrodes implanted in the brain at a plurality of locations to monitor electrical activity in the brain at the plurality of locations. In such implementations, the observed signal (e.g., sensor time-domain signal 201, FIG. 2a) obtained from each of sensor(s) 110 (e.g., intracranial sensor 110-2) represents the aggregate activity (e.g., corresponding to 10,000 neurons) in the region proximate to the respective sensor (e.g., intracranial sensor 110-2). In some embodiments, arrays of sensors (e.g., sensor(s) 110) are designed to produce a plurality of sensor time-domain signals (e.g., sensor time-domain signal 201, FIG. 2A). In such embodiments, each of the plurality of time-domain signals is normalized (e.g., normalized with respect to signal amplitude or power) and/or offset (e.g., by the addition or subtraction of a fixed signal value) relative to other time-domain signals in the plurality of time-domain signals. Statistical features of the plurality of time-domain signals, for example, obtained from arrays of sensors (e.g., Sensor(s) 110) are optionally used to enhance acoustic characteristics of the representations of a plurality of acoustic signals. For example, in some embodiments, an estimate of the "busiest" signal(s) (e.g., signals with the highest signal content) of the plurality of time domain signals (e.g., obtained from arrays of sensors (e.g., sensor(s) 110) at a plurality of distinct locations in a brain) is computed based on activity detected or computed using a sliding window Fourier transform. In such embodiments, the "busiest" signal(s) are used for method 400 (described herein with reference to FIGS. 4A-4C).

In some embodiments, the plurality of acoustic signals, each corresponding to one of the plurality of distinct locations in the brain (or, alternatively, to a particular sensor or set of sensors 110), comprise (504) audibly distinct acoustic signals. For example, the plurality of acoustic signals, each corresponding to one of the plurality of distinct locations in the brain, comprise audibly distinct pitch (e.g., base frequencies), different rates of vowel transition, different vibrato modulations, and/or different acoustic signal intensities (e.g., loudness of the acoustic signal). In some embodiments, the plurality of acoustic signals, each corresponding to one of the plurality of distinct locations in the brain, comprise (506) audibly distinct sonic identities. For example, as explained above, for a time-domain signal obtained from the left hemisphere in the brain, a sonic identity is selected corresponding to the sonic identity of (e.g., acoustic characteristics defining or associated with) a violin (or, more generally, a first "voice"); whereas for a time-domain signal obtained from the right hemisphere in the brain, a sonic identity is selected corresponding to the sonic identity of (e.g., acoustic characteristics defining or associated with) a guitar (or, more generally, a second "voice").

FIGS. 6A-6F are flowcharts representing a method 600 for sonifying electrical signals obtained from a living subject, in accordance with some embodiments. Method 600 is optionally governed by instructions that are stored in a computer readable storage medium and that are executed by a digital processor system (or, optionally, one or more digital processor systems) (e.g., digital processor system 160). Each of the operations shown in FIGS. 6A-6F optionally corresponds to instructions stored in a computer memory or non-transitory computer readable storage medium. The computer readable storage medium optionally includes a magnetic or optical disk storage device, solid state storage devices such as flash memory, or other non-volatile memory device or devices. The computer readable instructions stored on the non-transitory computer readable storage medium are in source code, assembly language code, object code, or other instruction format that is interpreted by one or more processors. For ease of explanation only, each of the operations shown in FIGS. 6A-6F is described as being executed by a digital processor system (e.g., digital processor 160, FIG. 1).

The digital processor system obtains (602) two or more time-domain signals, including at least one time-domain signal representing brain activity (e.g., electrical activity in the living subject's brain) and at least one time-domain signal representing heart activity (e.g., electrical activity in the living subject's heart), each of the one or more time-domain signals having a time-varying signal value. For example, at least one time-domain signal 218 (FIG. 2B) representing brain activity is obtained from a sensor 110 (FIG. 1) and at least one time-domain signal 218 (FIG. 2B) representing heart activity is obtained from a heartbeat/pulse sensor 112. In some embodiments, a sensor 110 (FIG. 1) and/or a heartbeat/pulse sensor 112 (FIG. 1) includes two or more sensing elements, and the corresponding time-domain signals 218 (FIG. 2B) each comprise a differential voltage signal between two of the two or more sensing elements.

In some embodiments, the at least one time-domain signal representing brain activity is obtained by conditioning (604) a sensor time-domain signal obtained from a sensor embedded in a particular location of a brain. For example, as shown in FIG. 1 and FIGS. 2A-2B, sensor time-domain signal 201 is sometimes obtained from a sensor embedded in a particular location of a brain (e.g., from intracranial sensor 110-2, FIG. 1) and—after optionally being pre-processed by analog front end 120/122 to produce filtered sensor time-domain signal 207—is conditioned by signal conditioning module 130/132.

Alternatively, in some embodiments, the at least one time-domain signal representing brain activity is obtained by conditioning (606) a first sensor time-domain signal obtained from a first dry-contact sensor; and the at least one time-domain signal representing heart activity is obtained by conditioning a second sensor time-domain signal obtained from a second dry-contact sensor. For example, as described with reference to FIG. 1 and FIGS. 2A-2B, a first sensor time-domain signal 201 (e.g., the first sensor time-domain signal) is sometimes obtained from a headband (e.g., the first dry-contact sensor is a headband or is embedded in a headband) with one or more metallic sensors (e.g., electrodes) that is worn by the living subject during use. A second sensor time-domain signal 201 (e.g., the second sensor time-domain signal) is sometimes obtained from a chest strap with one or more metallic sensors that is worn by the living subject during use. Alternatively, or in addition to, the second sensor time-domain signal 201 (e.g., the second sensor time-domain signal) is sometimes obtained from a thumb apparatus or a hand apparatus with one or more metallic sensing elements (e.g., electrodes) that are touched (e.g., with the living subject's thumbs) and/or held onto (e.g., with the living subject's hands) by the living subject during use. After optionally being pre-processed by analog front end 120/122 to produce filtered sensor time-domain signal 207—time-domain signals 201 are conditioned by a signal conditioning module 130/132.

In some embodiments, the conditioning of a respective sensor time-domain signal includes (608) upsampling the respective sensor time-domain signal to produce an intermediate signal and low pass filtering the intermediate signal to produce a respective time-domain signal. For example, as shown in FIG. 2B, filtered sensor time-domain signal 207—after conversion from an analog signal to a corresponding digital signal—is upsampled (e.g., by upsampler 212, FIG. 2B) to produce a first intermediate signal (e.g., first intermediate signal 214, FIG. 2B). For example, as explained above, if the original sampling rate of the digital representation of the analog filtered sensor time-domain signal corresponds to 500 Hz, the first intermediate signal (e.g., first intermediate signal 214) produced by upsampler 212 has a sampling rate used in conventional audio applications (e.g., 48 kHz). First intermediate signal 214 is then low pass filtered (e.g., by digital low pass filter(s) 216, FIG. 2B) to produce the time-domain signal or a signal corresponding to the time-domain signal (e.g., time-domain signal 218, FIG. 2B).

The digital processor system produces (610) representations of a plurality of acoustic signals. Each representation of an acoustic signal of the plurality of acoustic signals corresponds to a respective time-domain signal of the two or more time-domain signals. For each respective representation of an acoustic signal, the respective representation is produced by concurrently generating (612) a plurality of acoustic parameters, including a plurality of time-varying acoustic parameters.

In this context, parameters are "concurrently generated" even if they are literally generated serially by single-threaded processor, when the resulting parameters are used or applied concurrently for generating an audio signal, or a representation of an audio signal. Typically, two or more concurrently generated parameters are generated or updated in response to a stream of digital signal values corresponding to the respective time-domain signal.

One or more of the plurality of time-varying acoustic parameters is modulated in accordance with at least the signal value of the respective time-domain signal. For example, as explained above with reference to FIG. 2C, signal modulator(s) 140/142 (optionally included in digital processor 160) concurrently generate(s) a set of acoustic parameters, including a plurality of time-varying acoustic parameters. In some embodiments, as described in relation to FIG. 2C above, the plurality of acoustic parameters includes a vibrato or frequency-control parameter (e.g., frequency-control parameter 222-a), a vowel-control parameter (e.g., vowel-control parameter 222-b), and/or a time-varying amplitude or intensity-control parameter (e.g., intensity-control parameter 222-c). In some embodiments, the set of acoustic parameters includes a pitch-control parameter (e.g., pitch-control parameter 222-d) and/or a sonic identity parameter (e.g., sonic identity parameter 222-e).

Attention is now directed towards operations 614-646, through which the digital processing system generates the plurality of acoustic parameters, and controls properties and/or features of acoustic parameters, in accordance with various embodiments.

In some embodiments, for a respective acoustic signal of the plurality of acoustic signals, generating the plurality of acoustic parameters includes (614) generating a frequency-control parameter in accordance with the signal value of the time-domain signal. For example, as described above with reference to FIG. 2C, signal modulator(s) 140/142 (optionally included in a digital processor system) includes vibrato modulator 220-a, which generates frequency-control parameter 222-a.

In some embodiments, for a respective acoustic signal of the plurality of acoustic signals, generating the plurality of acoustic parameters includes (615) generating a frequency-control parameter by: obtaining (616) a base frequency corresponding to the respective acoustic signal; modulating (618) the base frequency in accordance with the signal value of the time-domain signal to produce a signal-dependent variation of the base frequency; and generating (620) the frequency-control parameter corresponding to the signal-dependent variation of the base frequency. For example, as explained above, vibrato modulator (e.g., Vibrato Modulator 220-a, FIG. 2C) generates a control parameter (e.g., a frequency control parameter) for controlling the amount of vibrato (which can be considered to be the amount of frequency variation) produced by a music or audio synthesizer. In some implementations (e.g., implementations in which pitch and vibrato are controlled during audio synthesis by separate parameters) the frequency-control parameter is independent of the base frequency or pitch, while in other implementations the frequency-control parameter incorporates the base frequency or pitch.

In some embodiments, for a respective acoustic signal of the plurality of acoustic signals, generating (622) the plurality of acoustic parameters includes generating a vowel-control parameter by selecting (624) a sequence of acoustic waveform patterns from a set of N acoustic waveform patterns. The set of N acoustic waveform patterns is arranged in a predefined order, where N is an integer greater than 2. In some embodiments, the sequence of acoustic waveform patterns includes (626) a sequence of vowel waveform patterns. The vowel-control parameter is further generated by modulating (628) a rate of selecting the sequence of acoustic waveform patterns in accordance with the signal value of the time-domain signal, to produce a signal-dependent rate of variation of acoustic waveform patterns. The vowel-control parameter is then generated (630) corresponding to the signal-dependent rate of variation of acoustic waveform patterns.

For example, as described above, vowel modulator (e.g., vowel-control parameter 222-b) modulates a rate of sequentially selecting acoustic waveform patterns from a set of 12 acoustic waveform patterns in accordance with the signal value of the time-domain signal (e.g., time-domain signal 218, FIG. 2C). For example, for an increase in signal value of the time-domain signal (e.g., time-domain signal 218), vowel modulator (e.g., vowel-control parameter 222-b) selects (e.g., scans through) a sequence of acoustic waveform patterns from a set of 12 acoustic waveform patterns more rapidly or at an increased rate; conversely, for a decrease in signal value of the time-domain signal (e.g., time-domain signal 218), vowel modulator (e.g., vowel-control parameter 222-b) selects (e.g., scans through) a sequence of acoustic waveform patterns from a set of 12 acoustic waveform patterns more gradually (e.g., slowly) or at a decreased rate.

In some embodiments, for a respective acoustic signal of the plurality of acoustic signals, generating the plurality of acoustic parameters includes (632): computing (634) a time-varying amplitude value in accordance with the signal value of the time-domain signal, and generating (636) a time-varying control parameter corresponding to the computed time-varying amplitude value.

For example, as described above in relation to FIG. 2C, an intensity modulator (e.g., intensity modulator 220-*c*, FIG. 2C) computes a time-varying amplitude value in accordance with the signal value of the time-domain signal (e.g., time-domain signal 218, FIG. 2C) and generates a time-varying intensity-control parameter (e.g., intensity-control parameter 222-*c*, FIG. 2C) corresponding to the computed time-varying amplitude value. In some implementations, for an increase in signal value of the time-domain signal (e.g., time-domain signal 218), the time-varying amplitude value—and corresponding time-varying intensity-control parameter (e.g., intensity-control parameter 222-*c*)—computed by intensity modulator (e.g., intensity modulator 220-*c*) increases. Conversely, for a decrease in signal value of the time-domain signal (e.g., time-domain signal 218), the time-varying amplitude value—and corresponding time-varying intensity-control parameter (e.g., Intensity-Control Parameter 222-*c*)—computed by intensity modulator (e.g., intensity modulator 220-*c*) decreases.

In some embodiments, for a respective acoustic signal of the plurality of acoustic signals, generating the plurality of acoustic parameters includes (632) selecting (638) a base frequency. The base frequency for each respective acoustic signal is (640) audibly distinct from the base frequency of any other acoustic signal of the plurality of acoustic signals. Generating the plurality of acoustic parameters further includes generating (642) a time-varying pitch-control parameter in accordance with the selected base frequency and the signal value of the time-domain signal. For example, as shown in FIG. 2C, signal modulator(s) 140/142 (optionally included in digital processor 160) include pitch modulator 220-*d*, which generates pitch-control parameter 222-*d* in accordance with a signal value of the time-domain signal (e.g., time-domain signal 218), and optionally in accordance with a selected base frequency (e.g., corresponding to a spatial location of sensing the time-domain signal).

In some embodiments, for a respective acoustic signal of the plurality of acoustic signals, generating the plurality of acoustic parameters includes (632) selecting (644) a sonic identity in accordance with a spatial location, with respect to the subject's body, of a sensor for sensing the time-domain signal. Generating the plurality of acoustic parameters further includes generating (646) an identity-control parameter in accordance with the selected sonic identity.

For example, as shown in FIG. 1, sensor(s) 110/112 are located at different spatial locations on the living subject's body (e.g., different spatial location in the brain, or on the skull, corresponding to EEG signals, or differential spatial location on the chest, arms, legs, or abdomen corresponding to ECG signals) for sensing the time-domain signal (e.g., sensor time-domain signal 201), and a sonic identity is selected in accordance with a spatial location on the body of the living subject. In this example, for a time-domain signal obtained from the left hemisphere in the brain, a sonic identity is selected corresponding to the sonic identity of (e.g., acoustic characteristics defining or associated with) a violin (or a first "voice"); for a time-domain signal obtained from the right hemisphere in the brain, a sonic identity is selected corresponding to the sonic identity of (e.g., acoustic characteristics defining or associated with) a guitar (or a second "voice"); and for a time-domain signal obtained from the heart, a sonic identity is selected corresponding to the sonic identity of (e.g., acoustic characteristics defining or associated with) a clarinet. In some implementations, the sonic identity is simply the base frequency of each generated acoustic signal (or representation of an acoustic signal), while in some other implementations, the sonic identity determines both the base frequency and one or more parameters (e.g., multipliers, offsets, etc.) that are used while generating the acoustic parameters corresponding to each time-domain signal (e.g., corresponding to each sensor signal being sonified). In some embodiments, a distinct sonic identity is selected in accordance with each lead of a multi-lead electrocardiogram (e.g., distinct from the sonic identity selected in accordance with any other lead of the multi-lead electrocardiogram or any other time-signal obtained).

Returning now to operation 610, each representation of an acoustic signal of the plurality of acoustic signals is further produced by combining (648) the concurrently generated plurality of acoustic parameters to produce the respective representation of the acoustic signal corresponding to the respective time-domain signal. For example, as shown in FIG. 2C, synthesizer module 150/152 (optionally included in digital processor 160) combines the concurrently generated set of acoustic parameters generated by signal modulator(s) 140/142 to produce a representation of an acoustic signal (representation of acoustic signal 230) corresponding to the time-domain signal (e.g., time-domain signal 218).

In some embodiments, combining the concurrently generated plurality of acoustic parameters includes (650) applying the concurrently generated plurality of acoustic parameters to a music synthesizer or music synthesizer module to produce the representation of an acoustic signal. In some embodiments, the music synthesizer or music synthesizer module uses (652) frequency modulation synthesis. For example, as shown in FIG. 2C, synthesizer module 150/152 uses frequency modulation synthesis implemented on frequency modulation synthesizer 224.

In some embodiments, the at least one time-domain signal representing brain activity includes (654) a plurality of time-domain signals representing brain activity at a plurality of distinct locations of a brain of the subject. Producing representations of a plurality of acoustic signals includes producing representations of three or more acoustic signals, each corresponding to the heart activity or one of the plurality of distinct locations of the brain of the subject. As described above, in some embodiments, the three or more acoustic signals are (or comprise) (656) audibly distinct acoustic signals. In some embodiments, the three or more acoustic signals include (658) audibly distinct sonic identities. For example, in some embodiments, the one or more time-domain signals representing brain activity include two or more time-domain signals representing brain activity including a first time-domain signal representing left lobe brain activity and a second time-domain signal representing right lobe brain activity.

In some embodiments, the digital processing system combines (660) the representations of each of the plurality of acoustic signals to produce a combined acoustic signal (e.g., using combiner module 170, FIG. 2D). In some embodiments, the combined acoustic signal, in audible form, manifests (662) one or more audibly discernible variations across a plurality of stages of an abnormal electrical event in the subject's body. For example, in some embodiments, the abnormal electrical event is (664) one of: an epileptic seizure, an ST-elevated myocardial infarction, a supraventricular tachycardia (SVT) event, an atrial fibrillation event, a ventral fibrillation event, a stroke, and/or an episode of fasciculation (i.e., muscle twitching).

In some other embodiments, audio signals corresponding to the aforementioned two or more representations of acoustic signals, are combined to produce a combined audio signal. For example, the combined acoustic signal, corresponding to representations of the plurality of acoustic signals, is generated (e.g., generated "in the air") by concurrent production of two or more individual acoustic signals within a physical space or in a manner that enables the concurrently produced acoustic signals to be heard concurrently by a human listener. Alternatively, audio signals corresponding to the aforementioned two or more representations of acoustic signals, are recorded on separate tracks, or directed to distinct speakers, for concurrent production as acoustic signals. In some embodiments, a plurality of acoustic signals, each corresponding to one of more of the aforementioned representations of acoustic signals, are recorded on distinct tracks, where the distinct tracks are configured to enable concurrent playback of the acoustic signals recorded in those tracks.

In some embodiments, the abnormal electrical event is a supraventricular tachycardia (SVT) event and the audible form of the combined acoustic signal is provided to the living subject (e.g., as sound output by headphones or a speaker system) as a feedback mechanism for the subject while the subject undergoes vagal maneuvers to quell the SVT event. In some embodiments, the event is a stroke and the acoustic form of the combined acoustic signals is provided to field medical personnel (e.g., paramedics, emergency medical technicians, and the like) as a manner through which a working differential diagnosis can be ascertained to differentiate between, for example, an ischemic stroke, a hemorrhagic stroke, a diabetic emergency, etc.

Alternatively, in some embodiments, the living subject is under the effects of anesthesia. The combined acoustic signal, in audible form, is provided to a doctor (e.g., an anesthesiologist) so that the doctor can determine a depth of the effects of the anesthesia. If the patient is not sufficiently anesthetized, the nervous system's response to an incision can generate an immediate response in the combined signal which may be more evident to the doctor than, for example, a displayed signal on a computer monitor.

Alternatively, or in addition to, in some embodiments, the combined acoustic signal, in audible form, manifests one or more audibly discernible variations of the subject's response to an external stimulus (e.g., visual and/or aural stimuli). For example, in some embodiments, the external stimulus is a video game, physical game, and/or exercise, and the combined acoustic signal is provided to the subject as a custom soundtrack.

While method 600 has been described with reference to at least one time-domain signal representing brain activity and at least one time-domain signal representing heart activity, one of ordinary skill in the art will recognize that either or both of the at least one time-domain signal representing brain activity and/or at least one time-domain signal representing heart activity may be replaced by a time-domain signal representing another bodily function. For example, in various embodiments, the at least one time-domain signal representing brain activity and/or at least one time-domain signal representing heart activity may be replaced by one of: a pulse oximetry signal, a capnography signal, a photoplethysmography signal, an electroencephalography (EEG) signal, and/or an electromyography (EMG) signal. Alternatively, one of ordinary skill in the art will recognize that method 600 may modified to make use of at least one time-domain signal representing brain activity, at least one time-domain signal representing heart activity, and at least one time-domain signal representing neither heart activity nor brain activity.

Squelching

Figure 7:
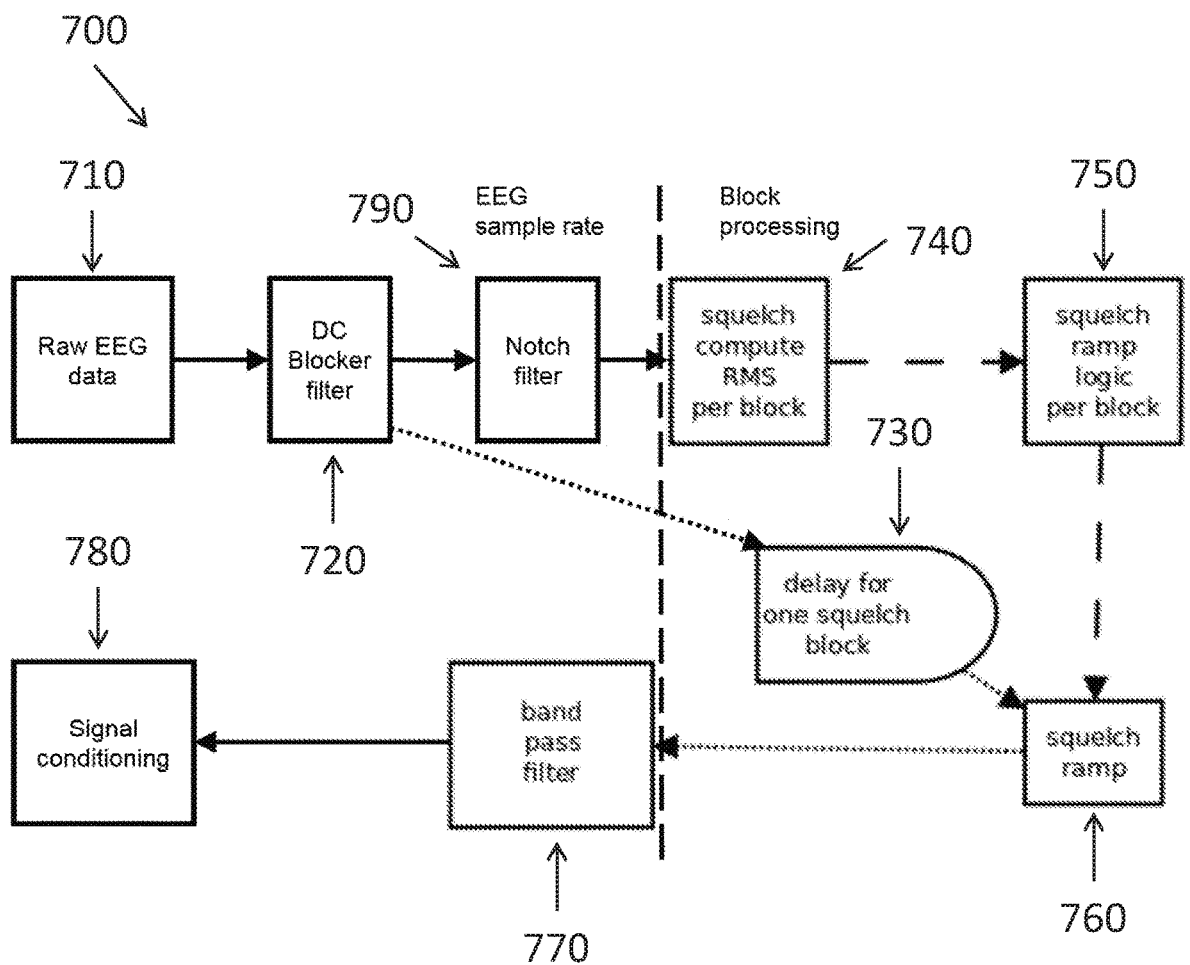
FIG. 7 includes a flow chart illustrating a method for squelching sonified signals obtained from a living subject, in order to suppress artifacts, in accordance with some embodiments.

Embodiments of the present disclosure may include a squelch feature for preventing the sonification of noisy signals, since in some cases these could be mistaken for signs of pathology (for example, in the case of EEG, a seizure). FIG. 7 shows an exemplary method 700 of squelching bioelectrical signals. When the squelch activates, the input to the sonification module (for example, any of the signal conditioning modules described herein, which may be used in a signal conditioning step 780 of method 700 in FIG. 7) may be ramped down to zero (such as with a squelch ramping step 760 of method 700 in FIG. 7), so that only a baseline audio "hum" tone is output. When the squelch deactivates, the input signal may be ramped back up to full (step 760). The method 700 may include the use of squelch ramp logic in a step 750 to determine when to activate or deactivate the squelch (step 760). These ramp functions can prevent abrupt changes in the output audio while also suppressing noise.

The method 700 may include a step of inputting raw data, such as raw EEG data, in a step 710. In many embodiments, the power of noisy signals such as those with noise caused by electrical interference or electrode movement is greater than the power of the raw, naturally-occurring bioelectrical signals such as EEG, including pathological signals. The squelch function (step 760) may therefore be activated (step 750) based on the root mean square (RMS) voltage of the raw input signal over a series of samples. The method 700 may include a step 740 of computing RMS per sample block before activating the squelch with the step 750. For example, if the RMS of a 160 ms sample block (40 consecutive samples at 250 samples per second) is greater than 100 μV, the signal can be assumed to be noisy, and the squelch may be activated. To achieve an RMS value of 100 μV, the raw signal could for example have an amplitude greater than 300 μV for longer than 17 ms, a value greater than 200 μV for longer than 40 ms, or a value greater than 100 μV for the full block duration of 160 ms.

The RMS calculation and squelch logic (steps 740, 750) may be performed when a full block of data samples has been collected, as opposed to on a sample-by-sample basis, to reduce processor load. As shown in FIG. 7, for example, the squelching ramp (step 760) is delayed (step 730) until a full sample block for squelching is received. To further reduce processor load, the sum of squared samples can be compared to the squared threshold multiplied by the number of samples in a block; this can be mathematically equivalent to comparing the RMS to the threshold, but avoids two operations per evaluation:

$$\sqrt{\frac{\sum_N (sample^2)}{N}} \geq threshold \rightarrow \sum_N (sample^2) \geq N \cdot threshold^2$$

The data samples used for squelch calculations can be taken after the raw signal, or in some embodiments, the notch-filtered signal, has been passed through a DC blocking high-pass filter (step 720). This can guarantee a baseline of 0 μV for the RMS calculation, and can ensure that the squelch function (step 760) will operate properly regardless of the actual DC offset present in the measurement. The samples may be taken before the sonification band-pass filter (step 770) to avoid false squelch triggers due to the filter ringing from high-amplitude voltage excursions.

The data samples used for squelch calculations can also be taken after the raw signal or DC-blocked signal has been passed through a notch filter (step 790). This can ensure that squelch calculations will not be affected by interference from sources such as mains power. Typical notch filter center frequency values can include 50 Hz and 60 Hz.

Figure 10:
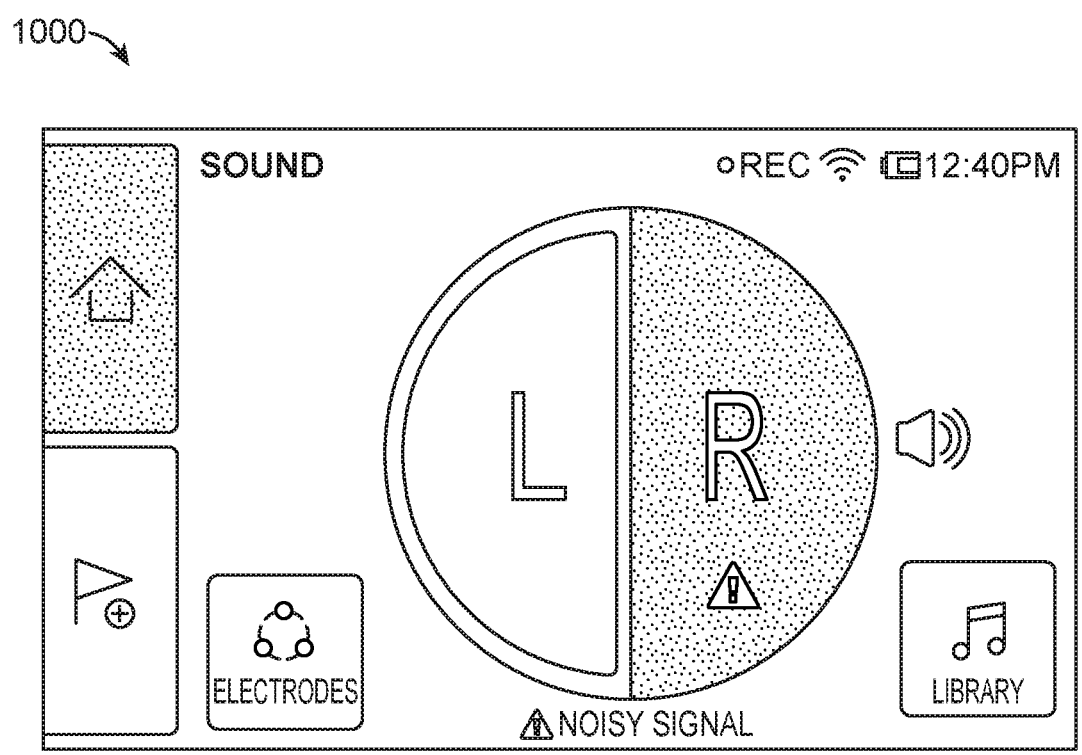
FIG. 10 shows an example of a graphical user interface indicating that the sonified signal is currently being squelched due to a noisy signal in a particular hemisphere of the brain, in accordance with some embodiments.

The user of the system can be visually notified on the user interface of the detection of a noisy signal in the selected sonified channel whenever the squelch is activated. FIG. 10 shows, for example, an example of a graphical user interface 1000 indicating that the sonified signal is currently being squelched due to a noisy signal in a particular hemisphere of the brain, in accordance with some embodiments.

Although the above steps show method 700 of squelching a bioelectrical signal in accordance with many embodiments, a person of ordinary skill in the art will recognize many variations based on the disclosure herein. The steps may be completed in a different order, steps may be added or omitted, some steps may comprise sub-steps, and/or many of the steps and/or sub-steps may be repeated as often as beneficial.

One or more of the steps of the method 700 may be performed with the hardware components and circuitry as described herein, for example, one or more of the processors, microprocessors, controllers, microcontrollers, and the like as described herein. The hardware components and circuitry may be programmed to provide one or more steps of the method 700, and the program may comprise program instructions stored on a computer readable memory or programmed steps of the logic circuitry such as a programmable array logic or a field programmable gate array.

Equalization Filter.

Figure 8:
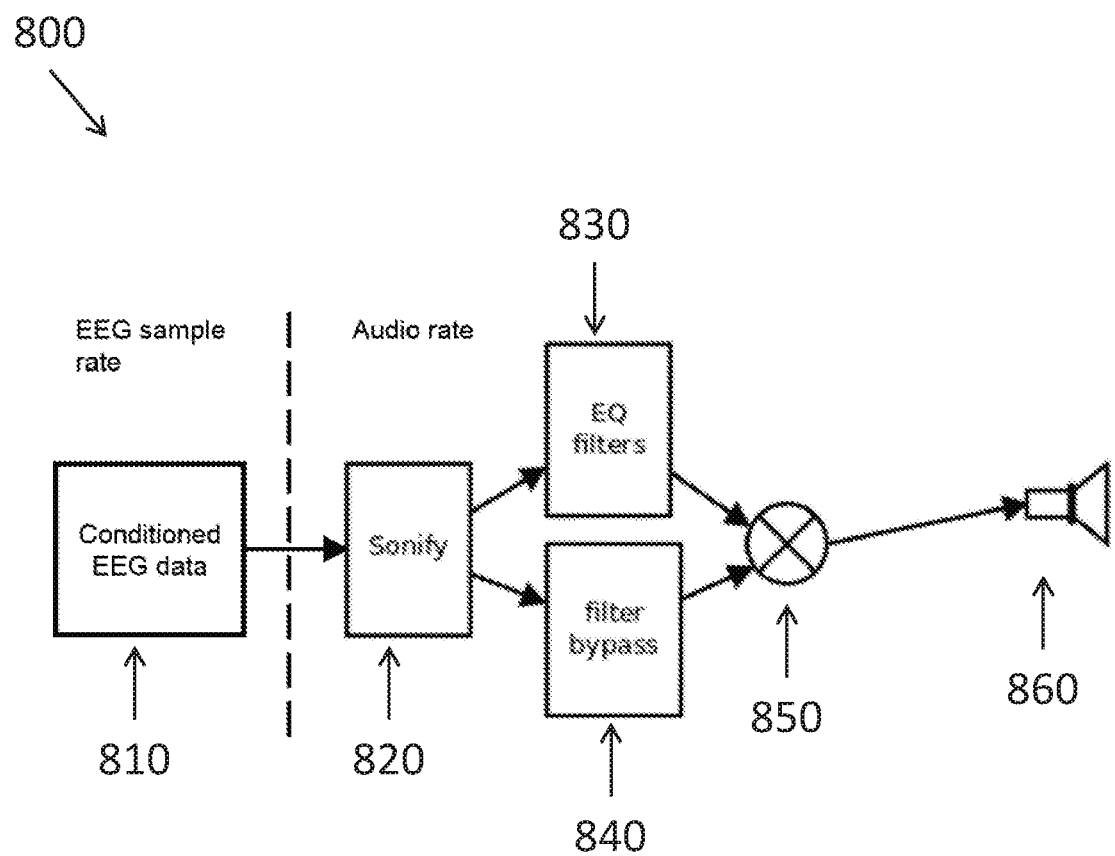
FIG. 8 includes a flow chart illustrating a method of implementing an audio equalization filter for sonified signals obtained from a living subject, in accordance with some embodiments.
Figure 9:
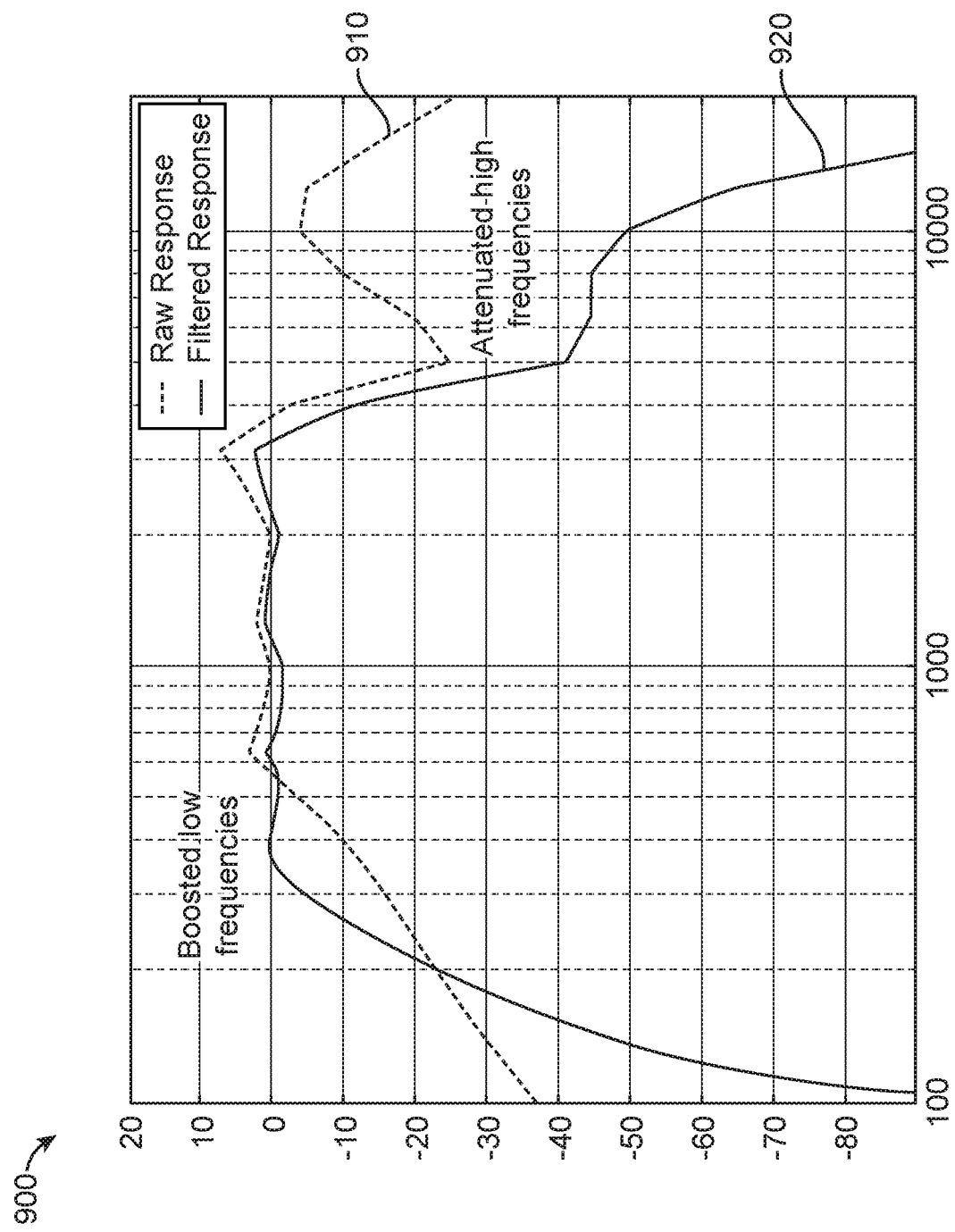
FIG. 9 shows a frequency spectrum chart comparing raw speaker frequency response and speaker frequency response adjusted with an equalizer, in accordance with some embodiments.

FIG. 8 shows a method 800 comprising the final steps of the sonification process. The method 800 may comprise a step 810 of providing conditioned bioelectrical signal data such as EEG data and a step 820 of sonifying the signal data as described herein. In many embodiments, the final step of the sonification process is passing the raw audio output through an EQ (equalization) filter(s) (step 830). This filter can compensate for the combined frequency response of the speaker(s) and device enclosure to adjust the overall output audio spectrum to be closer to ideal, for example boosting low frequencies so that the overall response is flattened. FIG. 9, for example, shows a frequency spectrum chart 900 (with the horizontal axis showing frequency in Hz and the vertical axis showing sound level in dB) comparing raw speaker frequency response spectrum 910 compared with adjusted speaker frequency response 920. FIG. 9 shows that low frequencies may be boosted and high frequencies attenuated. In many embodiments, the sonification is based on a human voice model, and adding the equalizer filter improves the device audio output in the human vocal range and allows for better audio contrast and improved detectability for pathological sounds. The equalizer filter can allow the device(s) described herein to use a more compact speaker to save power and space in the physical design, but still achieve sufficiently loud and accurate audio.

The equalizer filter may be implemented as a digital filter running in the device firmware. Filtering can run at the audio rate, at the last stage of sonification. In some embodiments, at least a portion of the signal may not need equalization and the equalizer may be bypassed in a step 840 instead. The final audio output that is sent to the audio digital to analog converter (DAC) 850 may comprise of a mix of raw and filtered audio samples, and, this may be achieved as part of the overall filter function. In a step 860, the speaker may then play the final audio output.

One or more of the steps of the method 800 may be performed with the hardware components and circuitry as described herein, for example, one or more of the processors, microprocessors, controllers, microcontrollers, and the like as described herein. The hardware components and circuitry may be programmed to provide one or more steps of the method 800, and the program may comprise program instructions stored on a computer readable memory or programmed steps of the logic circuitry such as a programmable array logic or a field programmable gate array.

Sound Libraries.

The systems and devices described herein, such as the body interface system 100, may further provide a library of examples of normal and pathological sonified bioelectrical signals, for example a library of normal and pathological (e.g., seizure) sonified EEG signals, for educational and demonstrational purposes. A sound library feature may be provided to allow playback of the stored example audio. For example, referring to FIG. 3A, the sound library source data may be stored in local data storage 170 of the digital processor system 160 or another memory coupled to the CPU 320 of the system 160. In some embodiments, the system may be in communication with a server or other database to access (and download, for example) additional library source data. The sound library source data may be stored on device itself as raw (e.g., EEG) signal data and may be sonified as described herein in the same way as a live (e.g., EEG) signal. Storing the signal data in this manner can provide a large memory savings when compared to storage as audio data (e.g., 32x for uncompressed audio).

Figure 11:
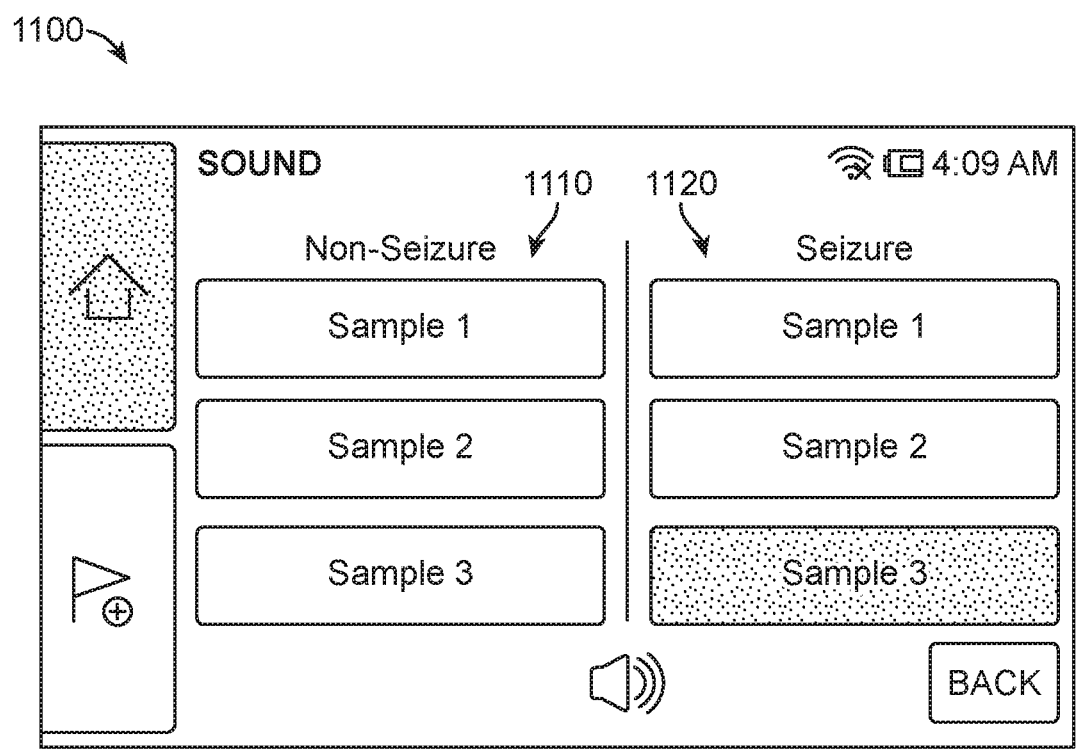
FIG. 11 shows an example of a graphical user interface for selecting from a number of stored data samples to sonify, including samples of normal and pathological brain activity, in accordance with some embodiments.

FIG. 11 shows an example of a graphical user interface 1100 for selecting from a number of stored data samples to sonify, including samples of normal brain activity 1110 (e.g., non-seizure) and samples of pathological brain activity 1120 (e.g., seizure).

Figure 12:
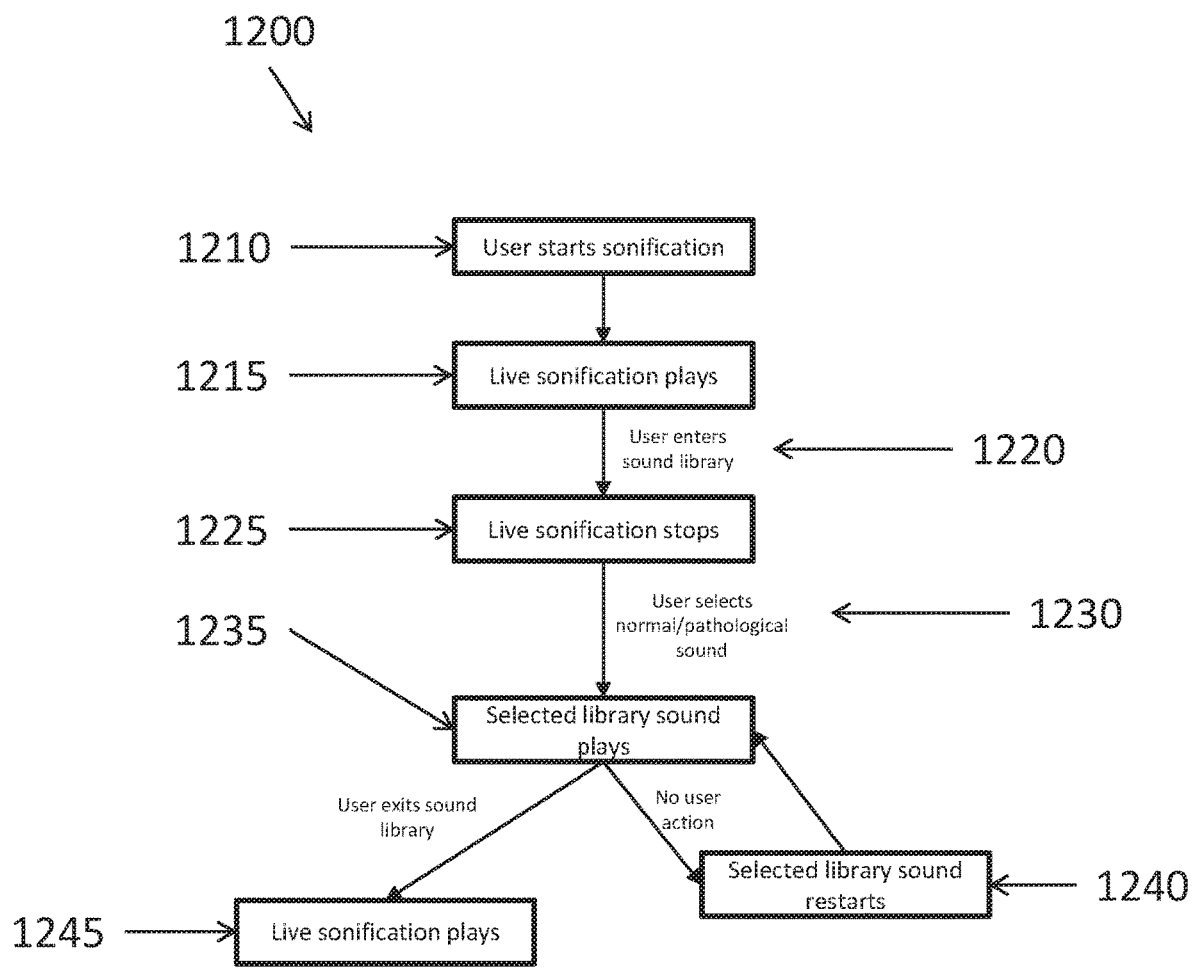
FIG. 12 includes flow chart illustrating a method of recording and sonifying a measured biological signal and comparing the sonified signal with a sample from a sound library, in accordance with some embodiments.

FIG. 12 shows a flow chart of a method 1200 for recording and sonifying a bioelectrical signal and comparing the sonified signal with a sample from a sound library. In a step 1210, a user may start sonification of a bioelectrical signal. In a step 1215, the digital processing system 160 or other system may audibly play the sonified bioelectrical signal. In a step 1220, the user may enter the sound library in the digital processing system 160 or other system, such as by manipulating a user interface of the system. In a step 1225, the live sonification of the bioelectrical signal may be stopped, for example, in response to the sound library being entered. Live, audible playback of the sonified bioelectrical signal may be stopped as well. In a step 1230, the user may select a sample sonified bioelectrical signal from the library of sonified bioelectrical signal samples for playback and comparison. The user may compare the played sample with that of the live sonified biological signal from step 1215. The sample sonified signal may be a normal or a pathological sound. In a step 1235, the selected sample sonified signal may be audibly played. If the user takes no action, the selected sample may continue to play or restart in a step 1240. In some embodiments, the user may select a different sample for playback and comparison from the sound library after the first sample sonified signal is played. If the user exits the sound library, the live sonified biological signal from step 1215 may resume playing.

One or more of the steps of the method 1200 may be performed with the hardware components and circuitry as described herein, for example, one or more of the processors, microprocessors, controllers, microcontrollers, and the like as described herein. The hardware components and circuitry may be programmed to provide one or more steps of the method 1200, and the program may comprise program instructions stored on a computer readable memory or programmed steps of the logic circuitry such as a programmable array logic or a field programmable gate array.

Figure 13:
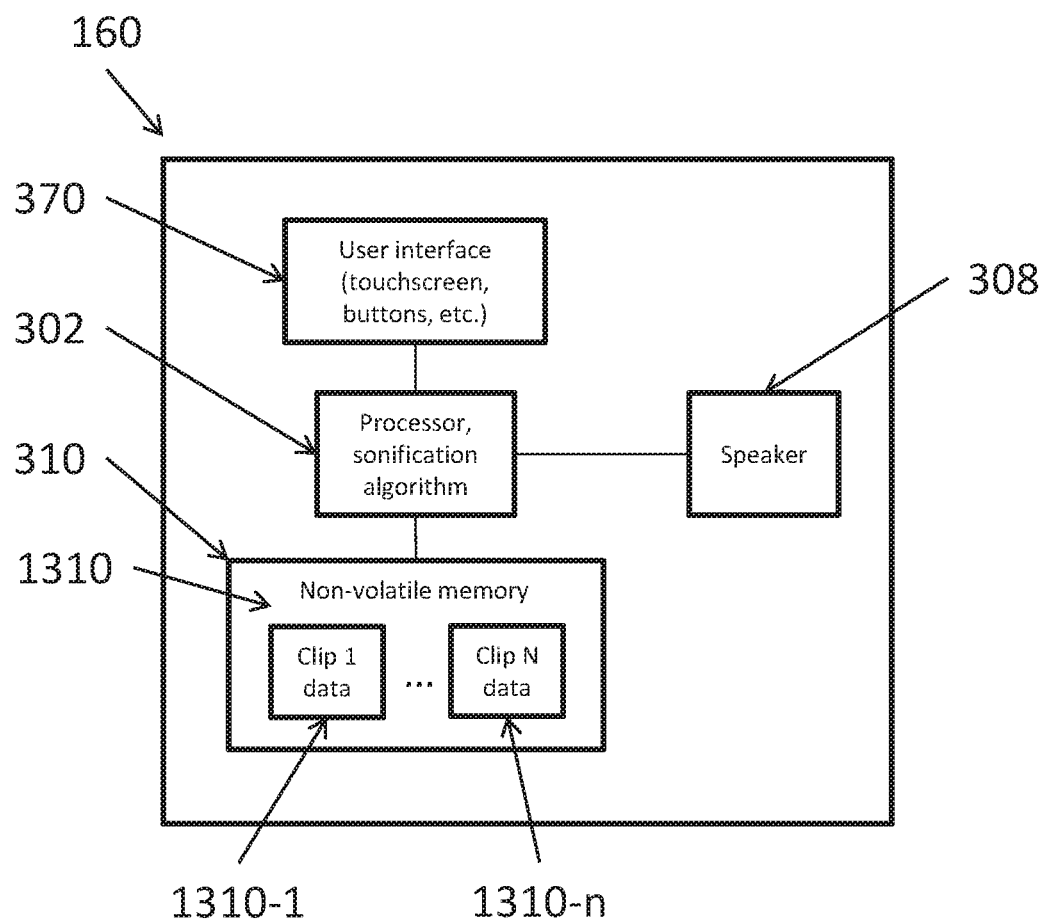
FIG. 13 shows a schematic diagram for a biological signal sonification device including a sound library, in accordance with some embodiments.

FIG. 13 shows a schematic diagram of the digital processor system 160 including a sound library 1310 stored in its memory 310. The system 160 may include a processor or CPU 302 to one or more of implement the sonification algorithm, access the sound library 1210, and output a signal to be played by the speaker 308. The system 160 may include a user interface 370 to control the processor to cause playback and/or access the sound library 1310. The sound library 1310 may include a plurality of samples of sonified bioelectrical signals, including sample 1310-1 to sample 1310-n. The samples may comprise samples of EEG signals, either with healthy or pathological patterns, that have been sonified. Some sample pathological EEG signals may include those with seizure, burst suppression, PLED (periodic lateralized epileptiform discharges), GPED (generalized periodic epileptiform discharges), or a triphasic pattern, to name a few.

Sonification Tagging.

In many embodiments, if the user starts the sonification function during a recording, the sonification device may automatically record a tag indicating that sonification was started, and, in cases where EEG is recorded, which hemisphere the signal being sonified originates from. Similarly, a tag may be added when sonification is stopped. These tags may include a timestamp to indicate when the action took place.

Figure 14:
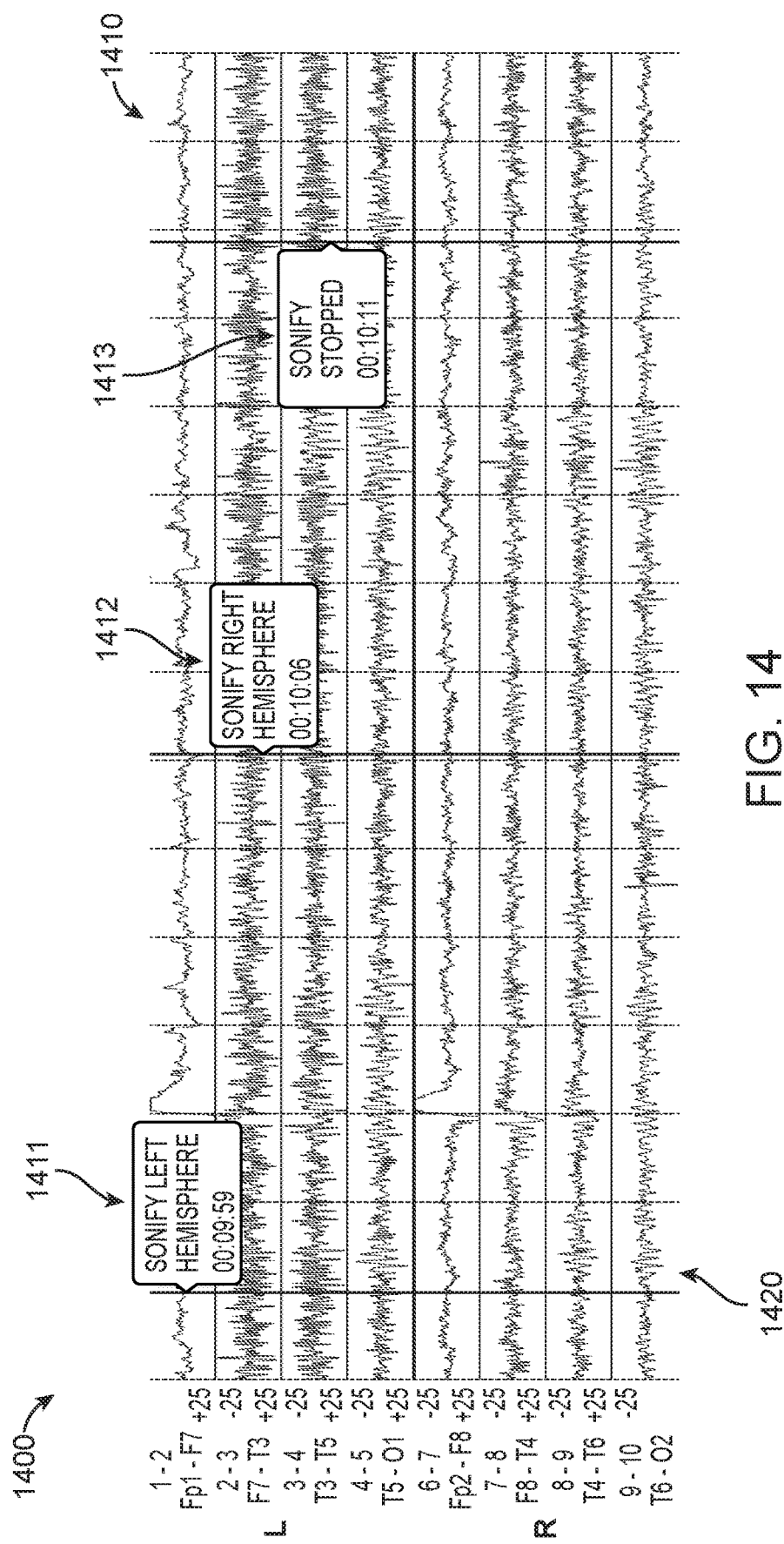
FIG. 14 shows a chart including a plurality of biological signal waveforms, which have been automatically tagged by the sonification device to indicate when and in which regions of the brain the user was sonifying, according to some embodiments.

Review software can read this tag when the raw signal data is loaded, and can indicate these events as an annotation on a waveform displayed, such as with the waveforms shown in FIG. 14. The chart 1400 in FIG. 14 includes a plurality of biological signal waveforms 1410, which have been automatically tagged (i.e., provided with tags 1411, 1412, 1413) by the sonification device to indicate when and in which regions of the brain the user was sonifying. The waveform reviewer can examine the state of the patient's target organ (e.g., brain) when the user is at the bedside was listening, for example, and can confirm any pathological events identified using sonification during that time. Tag data may include one or more time stamps, a user note on the pathology of the waveform, and an identifier for the note-maker, to name a few.

While preferred embodiments of the present disclosure have been shown and described herein, it will be obvious to those skilled in the art that such embodiments are provided by way of example only. Numerous variations, changes, and substitutions will now occur to those skilled in the art without departing from the scope of the present disclosure. It should be understood that various alternatives to the embodiments of the present disclosure described herein may be employed in practicing the inventions of the present disclosure. It is intended that the following claims define the scope of the invention and that methods and structures within the scope of these claims and their equivalents be covered thereby.

The invention claimed is:

1. A method of sonifying electrical signals obtained from a living subject, the method comprising:
   obtaining a time-domain signal representing activity of an organ of the living subject;
   determining a voltage of the time-domain signal over a time block;
   producing an acoustic signal based on the time-domain signal over the time block, the acoustic signal comprising one or more audibly discernible variations representative of activity of the organ of the living subject; and
   squelching the time-domain signal over at least a portion of the time-block as the acoustic signal is produced from the time-domain signal if the determined voltage is over a threshold voltage,
   wherein squelching the time-domain signal comprises ramping down the time-domain signal as an input to produce the acoustic signal, the time-domain signal being ramped down over the at least the portion of the time block.

2. The method of claim 1, wherein the organ of the living subject comprises a heart of the living subject, and wherein the one or more audibly discernible variations are representative of activity of the heart.

3. The method of claim 1, wherein the organ of the living subject comprises a brain of the living subject, and wherein the one or more audibly discernible variations are representative of activity of the brain.

4. The method of claim 1, further comprising audibly providing, with one or more speakers, the acoustic signal to the living subject for feedback therapy for the living subject or to a living person other than the living subject for determining activity of the organ of the living subject, the feedback therapy or the determining of the activity of the organ being based on the one or more audibly discernible variations.

5. The method of claim 1, wherein the acoustic signal is musical.

6. The method of claim 1, further comprising ramping up the time-domain signal as the input to produce the acoustic signal as the squelching is deactivated.

7. The method of claim 1, wherein the acoustic signal is produced by combining the time-domain signal and a baseline signal.

8. The method of claim 1, wherein the time-domain signal is squelched after the time-domain signal has been fully acquired over the time block.

9. The method of claim 1, wherein determining a voltage of the time-domain signal over the time block comprises determining a root mean square (RMS) of the time-domain signal over the time block.

10. The method of claim 9, wherein the RMS of the time-domain signal is determined after the time-domain signal has been fully acquired over the time block.

11. The method of claim 1, further comprising high-pass filtering a raw signal from the organ of the living subject to produce the time-domain signal.

12. The method of claim 1, wherein the time-domain signal comprises one or more of an ECG, EKC, EEG, ENG, or EMG signal.

13. A system for sonifying electrical signals obtained from a living subject, the system comprising:
    one or more processors; and
    a memory coupled to the one or more processors and comprising instructions for the one or more processors for:

obtaining a time-domain signal representing activity of an organ of the living subject;

determining a voltage of the time-domain signal over a time block;

producing an acoustic signal based on the time-domain signal over the time block, the acoustic signal comprising one or more audibly discernible variations representative of activity of the organ of the living subject; and squelching the time-domain signal over at least a portion of the time-block as the acoustic signal is produced from the time-domain signal if the determined voltage is over a threshold voltage, wherein squelching the time-domain signal comprises ramping down the time-domain signal as an input to produce the acoustic signal, the time-domain signal being ramped down over the at least the portion of the time block.

14. The system of claim 13, wherein the organ of the living subject comprises a heart of the living subject, and wherein the one or more audibly discernible variations are representative of activity of the heart.

15. The system of claim 13, wherein the organ of the living subject comprises a brain of the living subject, and wherein the one or more audibly discernible variations are representative of activity of the brain.

16. The system of claim 13, further comprising one or more speakers, wherein the instructions of the memory further instructs the one or more processors to audibly provide, with the one or more speakers, the acoustic signal to the living subject for feedback therapy for the living subject or to a living person other than the living subject for determining activity of the organ of the living subject, the feedback therapy or the determining of the activity of the organ being based on the one or more audibly discernible variations.

17. The system of claim 13, wherein the acoustic signal is musical.

18. The system of claim 13, wherein the instructions for the one or more processor further comprises a step of ramping up of the time-domain signal as the input to produce the acoustic signal as the squelching is deactivated.

19. The system of claim 13, wherein the one or more processors is instructed to produce the acoustic signal by combining the time time-domain signal and a baseline signal.

20. The system of claim 13, wherein the time-domain signal is squelched after the time-domain signal has been fully acquired over the time block.

21. The system of claim 13, wherein determining a voltage of the time-domain signal over the time block comprises determining a root mean square (RMS) of the time-domain signal over the time block.

22. The method of claim 21, wherein the one or more processors is instructed to determine the RMS of the time-domain signal after the time-domain signal has been fully acquired over the time block.

23. The system of claim 13, wherein the instructions of the memory further instruct the one or more processors to high-pass filter a raw signal from the organ of the living subject to produce the time-domain signal.

24. The system of claim 13, wherein the time-domain signal comprises one or more of an ECG, EKC, EEG, ENG, or EMG signal.

* * * * *